United States Patent
Gerbi et al.

(10) Patent No.: US 6,587,750 B2
(45) Date of Patent: Jul. 1, 2003

(54) REMOVABLE INFINITE ROLL MASTER GRIP HANDLE AND TOUCH SENSOR FOR ROBOTIC SURGERY

(75) Inventors: Craig Richard Gerbi, Mountain View, CA (US); Eugene F. Duval, Menlo Park, CA (US); Don Minami, Monte Sereno, CA (US); Bob Hager, Fort Collins, CA (US); J. Kenneth Salisbury, Atherton, CA (US); Akhil Madhani, Glendale, CA (US); John Stern, Menlo Park, CA (US); Gary S. Guthart, Mountain View, CA (US)

(73) Assignee: Intuitive Surgical, Inc., Sunnyvale, CA (US)

( * ) Notice: Subject to any disclaimer, the term of this patent is extended or adjusted under 35 U.S.C. 154(b) by 0 days.

(21) Appl. No.: 09/964,171

(22) Filed: Sep. 25, 2001

(65) Prior Publication Data

US 2003/0060927 A1 Mar. 27, 2003

(51) Int. Cl.$^7$ ................................................. G06F 19/00

(52) U.S. Cl. ............... 700/245; 700/246; 700/247; 700/248; 700/251; 700/258; 700/259; 700/260; 700/264; 600/102; 600/407; 600/427; 600/424; 600/429; 600/595; 606/1; 606/130; 606/139; 318/568.11; 318/568.12; 318/568.21; 318/568.25; 901/1; 128/897

(58) Field of Search ................. 700/57, 245, 247, 700/246, 255, 257, 248, 258, 264, 259, 251, 260; 600/102, 407, 427, 429, 424, 595; 606/1, 130, 139; 607/3, 9, 17; 128/897, 898, 923; 269/236, 297; 356/399; 379/88.14; 414/1; 318/568.11, 568.12, 568.21, 568.25; 901/1

(56) References Cited

U.S. PATENT DOCUMENTS

| | | | |
|---|---|---|---|
| 4,791,934 A | 12/1988 | Brunnett | |
| 5,187,796 A | 2/1993 | Wang et al. | |
| 5,217,003 A | * 6/1993 | Wilk | .................. 700/131 |
| 5,343,385 A | 8/1994 | Joskowicz et al. | |
| 5,427,097 A | 6/1995 | Depp | |
| 5,598,269 A | * 1/1997 | Kitaevich et al. | ............ 700/132 |
| 5,609,560 A | * 3/1997 | Ichikawa et al. | ............ 600/101 |
| 5,622,170 A | 4/1997 | Schulz | |

(List continued on next page.)

FOREIGN PATENT DOCUMENTS

| | | |
|---|---|---|
| WO | WO 96/09587 | 3/1996 |
| WO | WO 97/29690 | 8/1997 |
| WO | WO 97/43942 | 11/1997 |
| WO | WO 97/43943 | 11/1997 |
| WO | WO 97/49340 | 12/1997 |

OTHER PUBLICATIONS

Mack, Minimally invasive and robotic, 2001, Internet, pp. 568–572.*

Schaaf, Robotic surgery: The future is now, 2001, Internet, pp. 1–13.*

(List continued on next page.)

Primary Examiner—William A. Cuchlinski, Jr.
Assistant Examiner—McDieunel Marc
(74) Attorney, Agent, or Firm—TownsendTownsend&CrewLLP; Mark D. Barrish, Esq.

(57) ABSTRACT

An input device for robotic surgery mechanically transmits a grip signal across a first joint coupling a handle to a linkage supporting the handle. The handle is removable and replaceable, allows unlimited rotation about the joint, and may optionally include a touch sensor to inhibit movement of a surgical end effector when the hand of the surgeon is not in contact with the handle.

32 Claims, 13 Drawing Sheets

U.S. PATENT DOCUMENTS

| | | | |
|---|---|---|---|
| 5,695,500 | A | 12/1997 | Taylor et al. |
| 5,732,703 | A | 3/1998 | Kalfas et al. |
| 5,749,362 | A | 5/1998 | Funda et al. |
| 5,762,748 | A | 6/1998 | Banholzer et al. |
| 5,776,064 | A | 7/1998 | Kalfas et al. |
| 5,808,665 | A | 9/1998 | Green |
| 5,841,950 | A | 11/1998 | Wang et al. |
| 5,855,553 | A | 1/1999 | Tajima et al. |
| 5,855,583 | A | 1/1999 | Wang et al. |
| 5,871,017 | A * | 2/1999 | Mayer ................... 128/897 |
| 5,967,980 | A * | 10/1999 | Ferre et al. ............... 600/424 |
| 5,971,976 | A * | 10/1999 | Wang et al. ............... 700/258 |
| 5,999,840 | A | 12/1999 | Grimson et al. |
| 6,001,108 | A | 12/1999 | Wang et al. |
| 6,006,127 | A * | 12/1999 | Van Der Brug et al. .... 600/427 |
| 6,063,095 | A | 5/2000 | Wang et al. |
| 6,201,984 | B1 | 3/2001 | Funda et al. |
| 6,244,809 | B1 | 6/2001 | Wang et al. |
| 6,246,200 | B1 | 6/2001 | Blumenkranz |
| 6,368,332 | B1 * | 4/2002 | Salcudean et al. .......... 606/130 |

OTHER PUBLICATIONS

Rotmes et al., Digital trainer developed for robotic assisted cardiac surgery, no date, Internet, pp. 1–7.*

Parsell, Surgeons in U.S. perform operation on France via robot, 2001, Internet, pp. 1–5.*

SVI, Minimally invasive surgery, 1998, Internet, pp. 1–4.*

Howe et al., Robotics for surgery, 1999, Internet, pp. 211–242.*

Willet, Telesurgery, 2001, Internet, pp. 1–3.*

Richard, Emerging technologies for surgery in the $21^{st}$ century, 1999, Internet, pp. 1–9.*

Butner et al., A real–time system for tele–surgery, 2001, Internet, pp. 236–243.*

Lai et al., Evaluating control modes for constrained robotic surgery, 2000, Internet, pp. 1–7.*

Cavusoglu et al., A laparoscopic telesurgical workstation, 1999, IEEE/Internet, pp. 728–739.*

Lapietra et al., Will surgeons of the "Computer–game generation" Have an advantage in developing robotic skills?, 2001, Internet, pp. 26–30.*

Lazarevic, "Feasibility of a Stewart Platform with Fixed Actuators as a Platform for CABG Surgery Device" Master's Thesis, Columbia University, Department of Bioengineering, pp. 1–45.

Schenker et al., "Development of telemanipular for dexterity enhanced microsurgery" Second Annual International Symposium on Medical Robotics and Computer Assisted Surgery, Nov. 4–7, 1995, Baltimore, Maryland, USA, pp. 81–88.

World Wide Web document entitled"Jet Propulsion Laboratory" printed May 13, 1999, http://robotics.jpl.nasa.gov/people/hayati/Quarterly_Reports/FY96Q3/jpl/jpl.html.

* cited by examiner

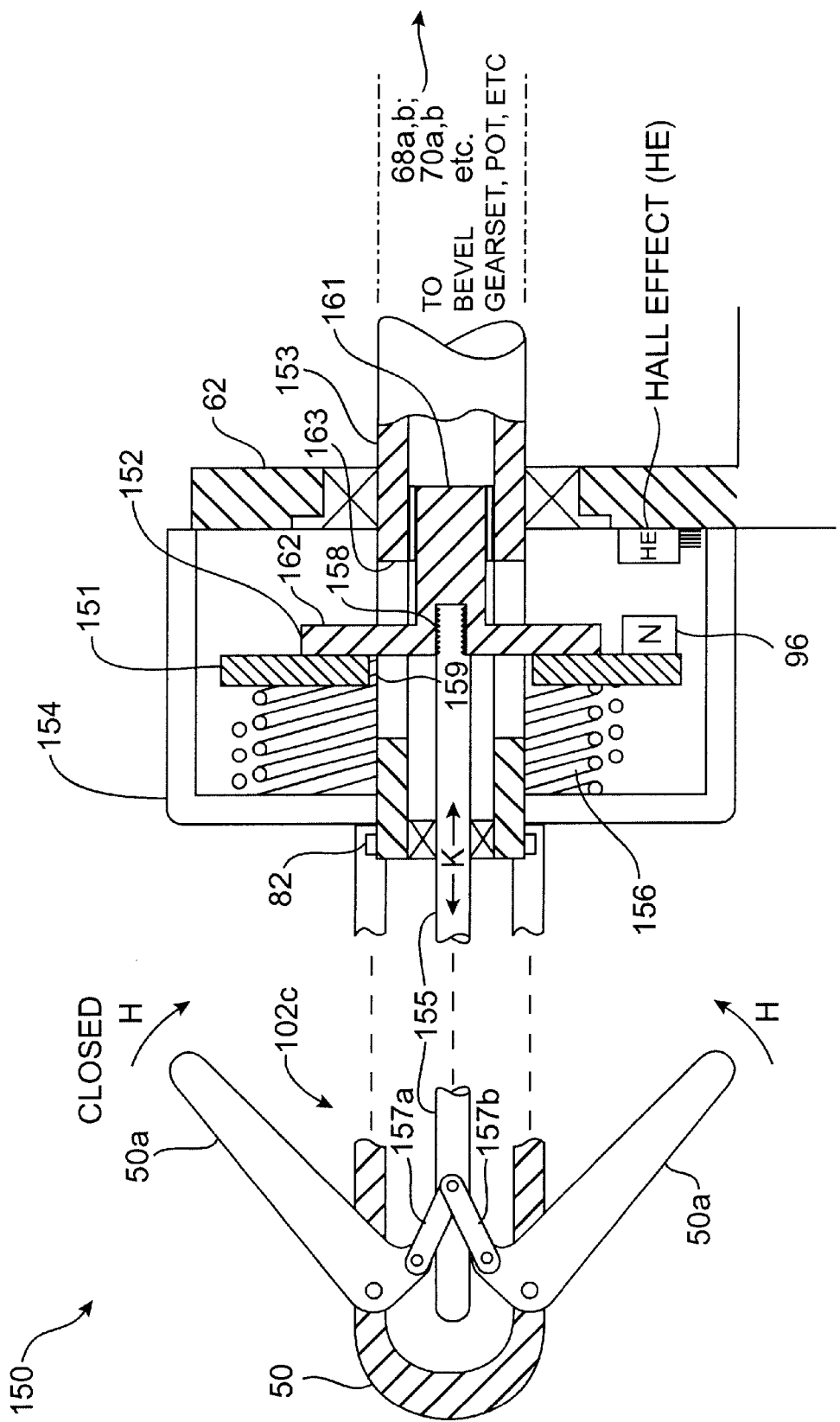

REMOVABLE INFINITE ROLL MASTER GRIP HANDLE AND TOUCH SENSOR FOR ROBOTIC SURGERY

CROSS-REFERENCES TO RELATED APPLICATIONS

The present application is related to pending U.S. patent application Ser. No. 09/287,858 filed Apr. 7, 1999, entitled "Alignment Of Master and Slave In A Minimally Invasive Surgical Apparatus" (now issued as U.S. Pat. No. 6,364,888), and to the corresponding International Application of the same title, published as WO 00/60421.

The present application is also related to pending U.S. patent application Ser. No. 09/433,120 filed Nov. 18, 1999, entitled "Cooperative Minimally Invasive Telesurgical System," and to the corresponding International Application of the same title, published as WO 00/30548.

The present application is also related to pending U.S. patent application Ser. No. 09/373,678, filed Aug. 13, 1999, entitled "Camera Referenced Control In A Minimally Invasive Surgical Apparatus" (now issued as U.S. Pat. No. 6,424,885), and to the corresponding International Application of the same title, published as WO 00/60521.

Each of the above noted patent applications are incorporated herein by reference.

BACKGROUND OF THE INVENTION

The present invention is generally related to input devices for use with robots and the like, and particularly to robotic surgical devices, systems, and methods. In an exemplary embodiment, the invention provides a surgical robotic input device which can input both movement (for example, by moving the handle in both translation and orientation), and actuation (for example, by variably squeezing first and second grip members together), and which allows unlimited rotation of the handle about an axis of the handle.

Advances in minimally invasive surgical technology could dramatically increase the number of surgeries performed in a minimally invasive manner. Minimally invasive medical techniques are aimed at reducing the amount of extraneous tissue that is damaged during diagnostic or surgical procedures, thereby reducing patient recovery time, discomfort, and deleterious side effects. The average length of a hospital stay for a standard surgery may also be shortened significantly using minimally invasive surgical techniques. Thus, an increased adoption of minimally invasive techniques could save millions of hospital days, and millions of dollars annually in hospital residency costs alone. Patient recovery times, patient discomfort, surgical side effects, and time away from work may also be reduced with minimally invasive surgery.

The most common form of minimally invasive surgery may be endoscopy. Probably the most common form of endoscopy is laparoscopy, which is minimally invasive inspection and surgery inside the abdominal cavity. In standard laparoscopic surgery, a patient's abdomen is insufflated with gas, and cannula sleeves are passed through small (approximately ½ inch) incisions to provide entry ports for laparoscopic surgical instruments. The laparoscopic surgical instruments generally include a laparoscope (for viewing the surgical field) and working tools. The working tools are similar to those used in conventional (open) surgery, except that the working end or end effector of each tool is separated from its handle by an extension tube. As used herein, the term "end effector" means the actual working part of the surgical instrument and can include clamps, graspers, scissors, staplers, and needle holders, for example. To perform surgical procedures, the surgeon passes these working tools or instruments through the cannula sleeves to an internal surgical site and manipulates them from outside the abdomen. The surgeon monitors the procedure by means of a monitor that displays an image of the surgical site taken from the laparoscope. Similar endoscopic techniques are employed in, e.g., arthroscopy, retroperitoneoscopy, pelviscopy, nephroscopy, cystoscopy, cisternoscopy, sinoscopy, hysteroscopy, urethroscopy and the like.

There are many disadvantages relating to current minimally invasive surgical (MIS) technology. For example, existing MIS instruments deny the surgeon the flexibility of tool placement found in open surgery. Most current laparoscopic tools have rigid shafts, so that it can be difficult to approach the worksite through the small incision. Additionally, the length and construction of many endoscopic instruments reduces the surgeon's ability to feel forces exerted by tissues and organs on the end effector of the associated tool. The lack of dexterity and sensitivity of endoscopic tools is a major impediment to the expansion of minimally invasive surgery.

Minimally invasive telesurgical robotic systems are being developed to increase a surgeon's dexterity when working within an internal surgical site, as well as to allow a surgeon to operate on a patient from a remote location. In a telesurgery system, the surgeon is often provided with an image of the surgical site at a computer workstation. While viewing a three-dimensional image of the surgical site on a suitable viewer or display, the surgeon performs the surgical procedures on the patient by manipulating master input or control devices of the workstation. The master controls the motion of a servomechanically operated surgical instrument. During the surgical procedure, the telesurgical system can provide mechanical actuation and control of a variety of surgical instruments or tools having end effectors such as, e.g., tissue graspers, needle drivers, or the like, that perform various functions for the surgeon, e.g., holding or driving a needle, grasping a blood vessel, or dissecting tissue, or the like, in response to manipulation of the master control devices.

While the proposed robotic surgery systems offer significant potential to increase the number of procedures that can be performed in a minimally invasive manner, still further improvements are desirable. In particular, known robotic input or master control devices do not generally provide a surgeon with the freedom of movement that may be available in open surgery. While existing input devices such as three-dimensional joysticks, exoskeletal gloves, and the like, provide significant freedom of movement in both orientation and translation within a virtual workspace, the structures often impose limits on the total amount of rotation. More specifically, surgeons in both open and minimally invasive surgical procedures are free to release a handle of a surgical device in one orientation and grasp it an alternative orientation. This releasing and re-grasping may occur several times during a procedure, so that the surgical instrument is, in total, rotated several times about its axis. Work in connection with the present invention has indicated that the limited rotation capabilities of known robotic surgical input devices can be a source of delay of the surgical procedure.

Still further refinements in input devices for robotic surgery would be desirable. For example, it is generally desirable to avoid inadvertent movement of a surgical end effector. Additionally, it is generally desirable to provide differing input devices for use with different surgical end effectors, or for use by differing surgeons or other system operators.

In light of the above, it would generally be desirable to provide improved input devices for directing movement of robots, and particularly for use in robotic surgery.

SUMMARY OF THE INVENTION

The present invention generally provides improved input devices, systems using such input devices, and related methods. In particular, the invention provides robotic systems having input devices that are particularly well suited for use in robotic surgery. The surgical input devices will often include a handle which can be both moved and actuated by a hand of a system operator. The hand will often actuate the handle by variably squeezing a pair of grip members together so as to articulate jaws of a surgical end effector, such as forceps, scissors, clamps, needle holders, and the like. Rather than sensing actuation of the handle with a sensor mounted on the handle itself, a signal may be transmitted from the handle to a sensor mounted on a linkage supporting the handle via one or more joints. The signal will preferably be sent using a mechanical actuation indicator which moves in response to the actuation input, the actuation indicator often comprising a compression rod which is arranged co-axially with an axis of rotation of the joint coupling the member to the handle. Advantageously, this arrangement can allow the sensor to detect actuation independent of movement about the joint, and also allows unlimited rotation of the handle. This arrangement also facilitates removal and replacement of the actuable handle, allowing alternative handles having differing characteristics to be mounted for different surgical end effectors, different system operators, different surgical procedures, or the like.

The invention also provides input devices which include sensors to verify that a hand of a system operator is in contact with the handle. Such a sensor can avoid inadvertent movement of the handle and surgical end effector, for example, when the linkage supporting the handle is accidentally bumped as the system operator is reaching for the handle.

In a first aspect, the invention provides a surgical robotic input device comprising a handle actuatable by a hand of an operator so as to define a variable actuation input. The handle is also moveable by the hand of the operator to define a movement input. A structural member supports the handle so that the handle is rotatable about an axis relative to the member. An actuation indicator extends from the handle toward the member. The indicator moves relative to the member in response to the actuation input. An input sensor is supported by the member. The input sensor generates a signal in response to movement of the indicator relative to the member. The input signal is independent of rotation of the handle about the axis.

Typically, the handle will pivotally engage the member at a joint which defines an axis. At least a portion of the indicator will often move co-axially with the axis when the handle is actuated. The handle and indicator will often be detachably coupled to the member and sensor, respectively, easing removal and replacement of the handle, particularly where the indicator comprises a compression rod. In the exemplary embodiment, the member is supported by a linkage providing six degrees of freedom, thereby allowing movement of the handle in both position and orientation. The actuation input will often comprise variably squeezing first and second grip members together.

In another aspect, the invention provides a surgical robotic apparatus for performing a surgical procedure on a patient body. The surgical apparatus robotically moves a surgical end effector so as to effect the surgical procedure in response to movement of an input handle by a hand of a system operator. The surgical robotic apparatus comprises a touch sensor system coupled to the handle. The touch system generates a first signal in response to coupling of the handle with the hand of the operator. The surgical robotic apparatus is enabled to an operative state in response to the first signal.

Typically, the surgical robotic apparatus will be reconfigured to an alternate state when the touch system generates a second signal. The touch system will generate this second signal in response to decoupling of the hand of the operator from the handle. The surgical robotic apparatus in the alternate state will inhibit movement of the end effector.

Optionally, the touch system may induce a vibration in the handle so as to sense coupling of the hand of the operator and the handle by measuring the induced vibration. In some embodiments, a piezoelectric element may be used to induce and/or sense the vibration. In other embodiments, one or more joint motors may be provided to drive a joint of a linkage supporting the handle, often to provide some force feedback to the operator of forces being imposed on the surgical end effector, for repositioning of the handles, or the like. The touch system may optionally induce a vibration in the handle by oscillating the joint motor, and can sense the induced oscillation using a joint actuation sensor. Such joint actuation sensors are often present for sensing handle movement inputs. The touch sensor system may be used in addition to other safety devices such as a view sensor system which can verify that the operator is viewing a display of the surgical site, typically by sensing whether the operator's head is disposed adjacent a binocular eye piece of a stereoscopic display system.

In another aspect, the invention provides a method for controlling a robotic system. The method comprises inputting commands to the robotic system by moving a handle of the robotic system with a hand of a system operator so as to articulate a pivotal joint. Commands are also input by actuating the handle with the hand. Movement of the handle is sensed by measuring articulation of the joint. Actuation of the handle is sensed by mechanically transmitting an actuation signal across the joint to an actuation sensor, and by measuring the mechanically transmitted actuation signal with the actuation sensor. An end effector is moved in response to the measured articulation of the joint, and in response to the measured actuation sensor.

Preferably, the mechanical transmitting step will comprise moving a compression rod co-axially with an axis of the joint. This facilitates movement of the handle about a handle support structure using a joint that can accommodate unlimited rotation of the handle. Such remote sensing of handle actuation also facilitates removal and replacement of the handle, often by handles having one or more differing characteristics.

In yet another aspect, the invention provides a robotic method comprising enabling an robotic apparatus to an operative state in response to coupling of a handle of the robotic apparatus with a hand of a system operator. Commands are input to the robotic apparatus by moving the handle with the hand of the operator. An end effector is moved in response to the input commands. The robotic apparatus is reconfigured to an alternate state in response to decoupling of the hand of the operator from the handle so as to inhibit inadvertent movement of the end effector. This is particularly advantageous when the handle moves in a plurality of degrees of freedom, as inadvertent bumping of the linkage supporting the handle will not lead to unintended movement of the end effector.

In one aspect of the invention, a master control input device is provided which is particularly advantageous for employment in master-slave robotic systems which benefit from orientational and/or positional alignment of a master device with respect to a corresponding associated slave device, and most particularly in robotic surgical systems which include an endoscope viewer or display. The master input device may be re-oriented in a roll degree of freedom without angular limit, thus permitting re-alignment following a large change in orientation of the slave with respect to the master, such as when a particular master device is switched from controlling a first robotic arm to controlling a second robotic arm. This aspect of the invention is also usefully employed in other systems involving alternative or complex associations of master and slave devices.

The International Application published as WO 00/60421 (incorporated by reference herein) describes, among other things, methods and devices for establishing a desired alignment or orientational relationship between a hand-held part of a master control and an end effector of an associated slave of a telerobotic system as viewed in an image displayed on a viewer. In an example comprising a typical robotic minimally invasive surgical system, the methods described therein provide for aligning an end effector of a slave surgical instrument, as shown in an endoscope image display or viewer, with a corresponding master handle operable by a surgeon.

One preferred method described in WO 00 60421 includes: causing the end effector to remain stationary; determining a current orientation of the end effector relative to a viewing end of an endoscope associated with the viewer; determining a desired corresponding orientation of the master handle relative to the viewer; and causing the master handle to be moved into the desired corresponding orientation. For example, this method permits the master and slave to be so aligned that the slave end effector appears to the operator in the viewer to be an extension of the master handle, a particularly intuitive or natural arrangement.

The methods described in WO 00 60421 extend to a control system arranged to cause the desired orientational relationship between the master handle and the end effector as viewed in the viewer, to be established and/or to be re-established or remapped when operative control between the master control and the slave has been interrupted. Examples include the removal of a surgical instrument from a robotic slave arm and the substitution of a new instrument, or another event which changes or disturbs the alignment, orientational and/or positional mapping of master to slave. Typically, the master handle will have more than one degree of freedom (DOF), one of which may be a handle roll DOF about a handle roll axis, which in turn operatively controls movement of an associated slave instrument about an instrument roll axis. Preferably, a desired orientational mapping of the roll DOF between master and slave is established or re-established by the methods described.

The International Application published as WO 00/30548 (also incorporated by reference herein) describes, among other things, methods and devices for selectably associating control effect for master/slave pairs in a robotic system. In an example comprising a typical robotic minimally invasive surgical system, the methods described therein provide for a surgeon using a particular master control handle to control more than one slave arm, e.g., by selectably switching the operative control effect of the master handle between a first slave arm and a second slave arm.

In one preferred surgical system embodiment described in WO 00 30548, a surgeon, in a cooperative operative procedure, may control an endoscope arm (by one of a number of alternative control means), may control a pair of left and right surgical instrument slave arms (using e.g., corresponding right and left hand master handles), and may also control at least one additional slave arm (e.g., using either the right or the left hand master handle) for at least one additional function, such as for stabilizing, retracting, or other functions benefiting from intermittent movement.

Following a large change in orientation of the slave with respect to the master, such as when a particular master device is switched or clutched from controlling a first robotic arm to controlling a second robotic arm, it may be desired to re-orient a master control device (e.g., a surgical system master handle) through a large roll angle, e.g., a roll angle of more than +/−90°.

In a case where control effect of the master is being switched from one slave instrument to another slave, a quick transition is beneficial to avoid interrupting the flow of the surgical procedure. If the range of roll motion of the master device is limited, a realignment of the master roll axis by more than +/−90° typically may require that the surgeon to let go of the master handle in order to re-grasp it at a more convenient angle. This can be slow and cumbersome, and may significantly interfere with the flow of the operation.

In addition, if the range of roll motion of the master device is limited, even if each individual master realignment upon transition or switching between slave instruments is comparatively small, the cumulative roll motion of the master device after several such transitions may reach the master roll limit, and frustrate further realignments (e.g., if the surgeon performs most of the sequential adjustments in the same direction).

Thus, by providing a master device with is not limited in roll motion, the invention allows master device roll realignments to occur without re-grasping the master and without interruption to the flow of the surgical procedure. Employing a preferred embodiment of the invention, such an roll axis adjustment to the master device optimally matches the slave roll range of motion to that of the master, so that the surgeon's motion is not restricted by the master joint roll limits. Thus the surgeon's control is only restricted by such roll limits as may be inherent in the particular associated slave instrument. In the event that the slave also is unrestricted in roll motion, the preferred master control device embodiments of the invention permit such a slave device to be used to optimal effect.

BRIEF DESCRIPTION OF THE DRAWINGS

FIG. 7C illustrates an alternative embodiment of a master control device having aspects of the invention, and which is similar in many respects to the examples of FIGS. 7A, 7B, and which has the sensor assembly mounted adjacent the master handle, proximal to the gimbal member, operated by a tension rod.

DESCRIPTION OF THE SPECIFIC EMBODIMENTS

Figure 1:
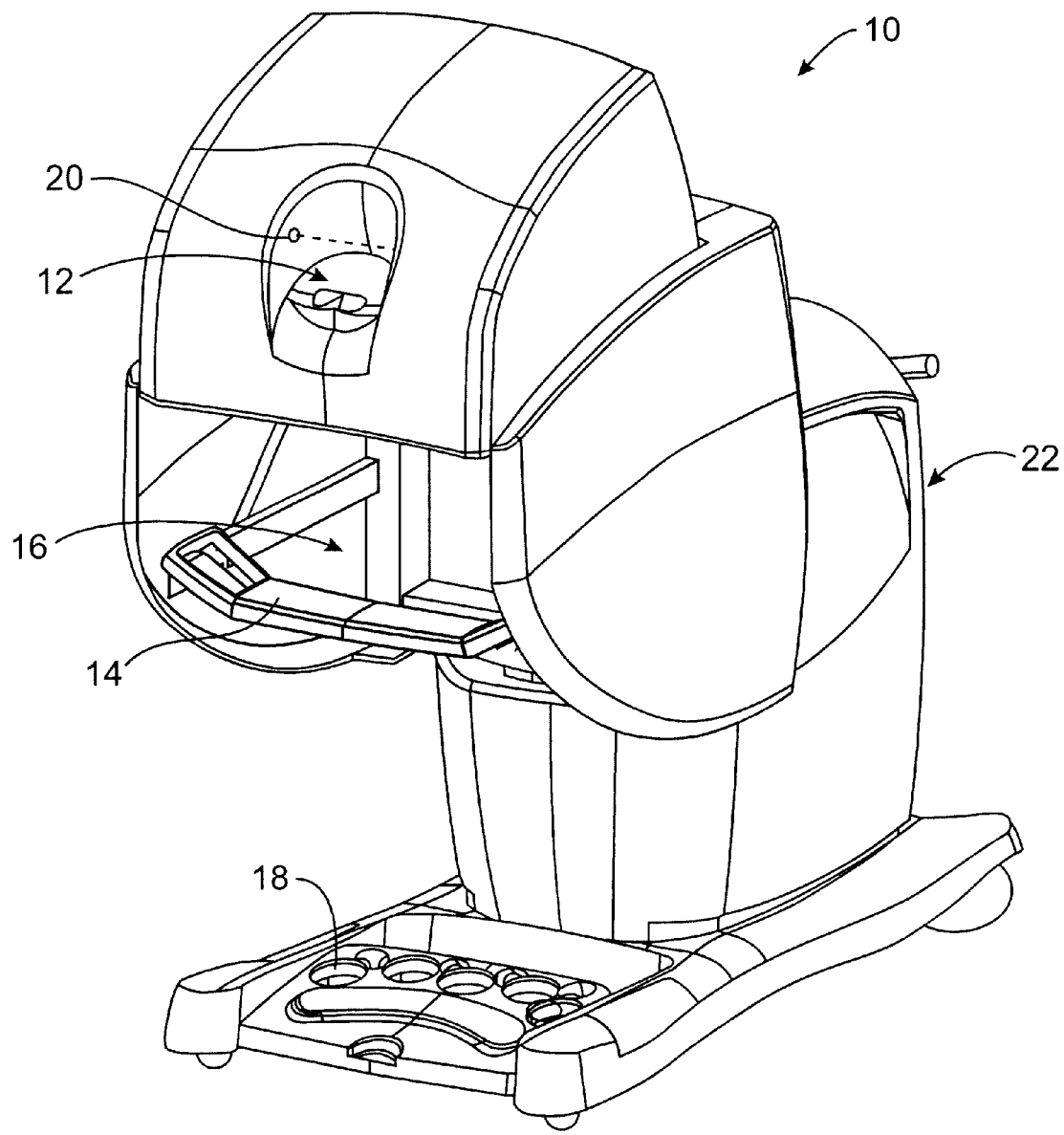
FIG. 1 is a perspective view of a robotic surgical control station.

Referring now to FIG. 1, a master control station 10 of a minimally invasive telesurgical system includes a viewer or display 12 where an image of a surgical site is shown. A support 14 can be used to rest the elbows or forearms of a system operator (typically a surgeon) while the system operator grips handles of an input device (see FIGS. 4 and 5), one in each hand. The handles are positioned in a master controller workspace 16 disposed beyond support 14 and below display 12. When using the control station, the operator typically sits in a chair in front of the control station, moves his or her head into alignment over the binocular display, and grips the input handles, one in each hand, while resting their forearms against support 14. This allows the handles to be moved easily in control space 16 in both position and orientation. Preferably, the system operator can alter the configuration of the telesurgical system using foot-operated input devices 18.

To ensure that the system operator is viewing the surgical site when the surgical end effectors move, control station 10 may include a viewing sensor 20 disposed adjacent display 12. More specifically, viewing sensor 20 may include a light signal generator such as an LED which directs an optical signal to a light sensor on an opposed side of display 12. When the system operator aligns his or her eyes with the binocular eye pieces of display 12 so as to view a stereoscopic image of the surgical worksite, the operator's head will block the optical signal from the light sensor. Hence, when the light signal is received by the light sensor, the system will often impede movement of the surgical end effector as described hereinbelow.

A processor 22 of control station 10 interprets movement and actuation of the input handles (and other inputs from the system operator or other personnel) so as to generate control signals effecting movement of the surgical end effectors and endoscope at the surgical worksite. Preferably, processor 22 will re-map the surgical worksite over controller workspace 16 so that the input handles in the hands of the system operator appear to the eyes of the system operator viewing the procedure through display 12 to be substantially connected to the end effectors of the surgical robotic tools. Control systems for providing this substantial connection are described in more detail in U.S. patent application Ser. No. 09/373,678 filed on Aug. 13, 1999, entitled Camera Referenced Control in a Minimally Invasive Surgical Apparatus, and published as corresponding PCT Publication WO 00/60521, the full disclosure of which are incorporated herein by reference.

Figure 2:
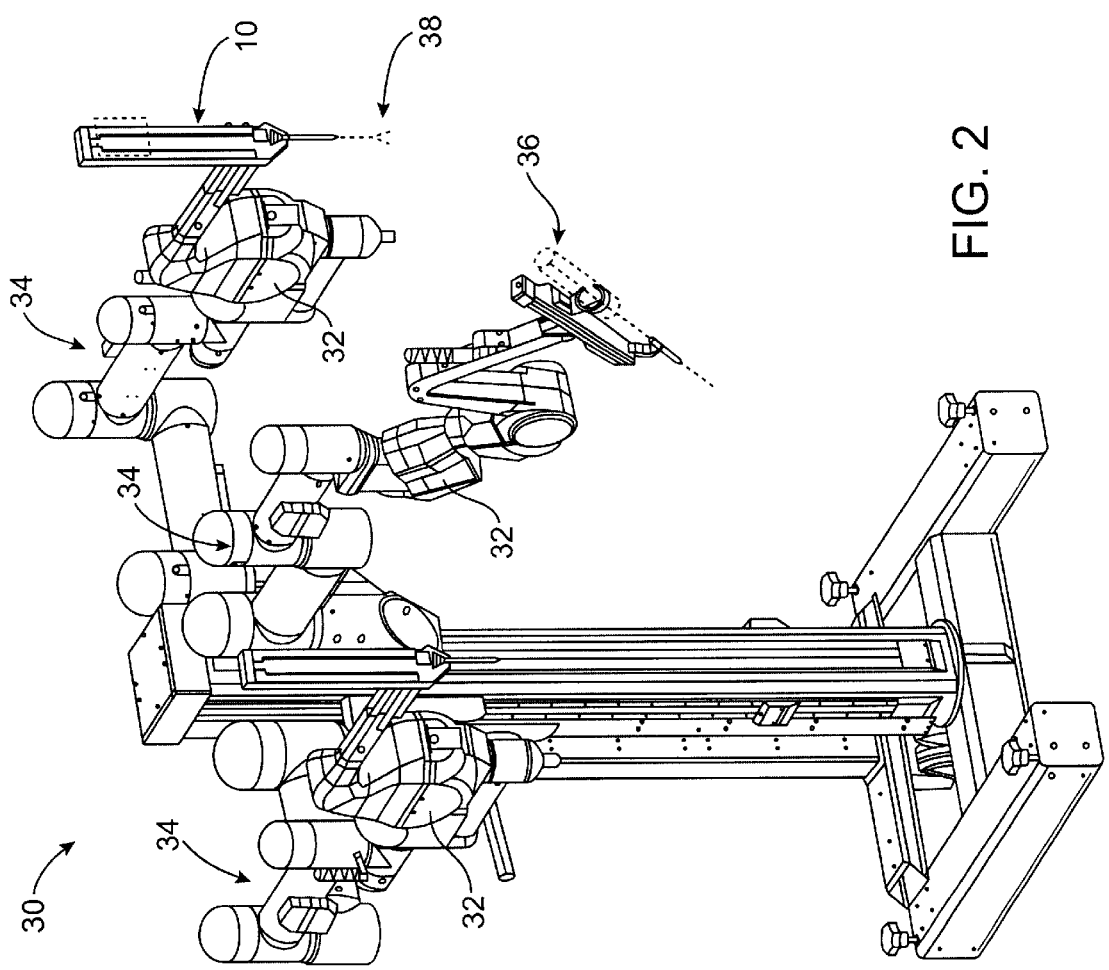
FIG. 2 is a perspective view of a cart having three robotic arms which move and actuate surgical end effectors of robotic surgical tools.

Referring now to FIG. 2, an exemplary robotic surgical arm assembly or cart 30 includes three robotic manipulator arms 32, with each manipulator arm supported by a manually positionable linkage referred to herein as a set-up joint 34. The central robotic manipulator 32 supports an endoscope 36, while the manipulators on either side of the endoscope have robotic surgical instruments 38 mounted thereon for manipulation of tissue.

Exemplary manipulators 32 include a linkage which constrains motion of the surgical tools mounted on the manipulator to rotation about a fixed location in space relative to the manipulator. By pre-positioning manipulators 32 relative to a minimally invasive aperture to an internal surgical site using set-up joints 34, and then locking the set-up joints in the aligned position, manipulators 32 can pivot elongate endoscopic robotic tools through a minimally invasive aperture to perform surgery within a patient body. Alternative manipulator structures are encompassed within the present invention, including those described in U.S. Pat. Nos. 5,878,193 and 5,184,601, the full disclosures of which are incorporated herein by reference, which position a proximal end of an endoscopic tool and allow the shaft of the endoscopic tool to pivot passively about the insertion point into the patient body. Still further alternative manipulator structures might be used within the scope of the present invention.

Figure 3:
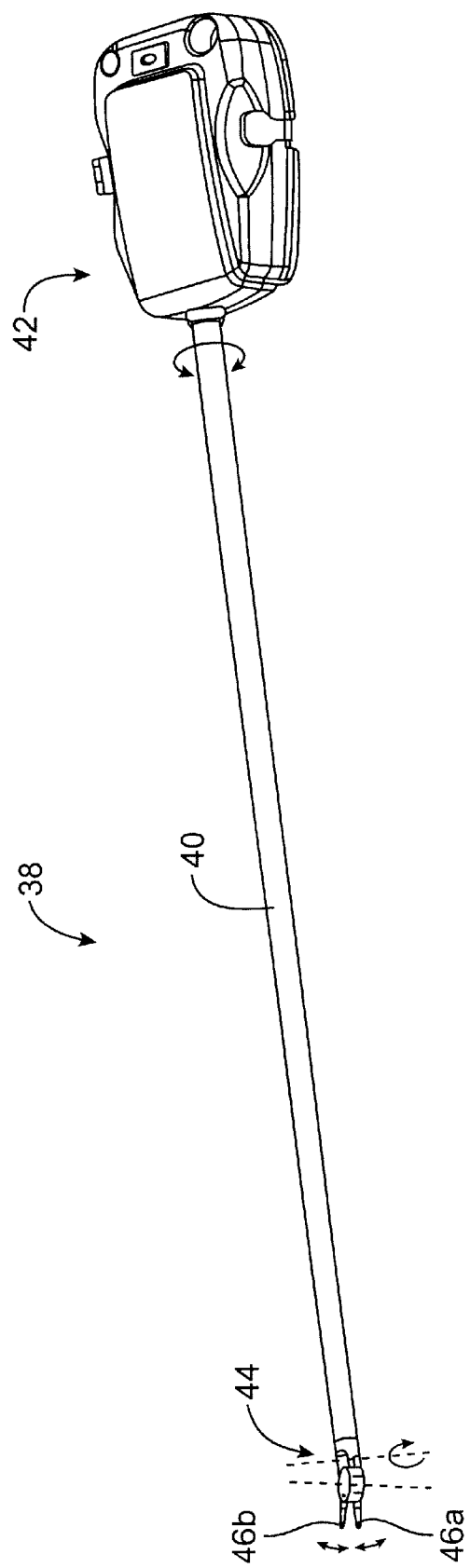
FIG. 3 is a perspective view of an exemplary robotic surgical tool.

FIG. 3 more clearly shows an exemplary robotic surgical instrument for manipulation of tissues. Instrument 38 includes an elongate shaft 40 extending from a proximal housing 42 to a distal joint or wrist 44. End effector elements 46a and 46b each move independently relative to wrist 44, so that the wrist and end effectors are provided with two degrees of freedom relative to shaft 40. To provide a full three orientational degrees of freedom to the end effector, shaft 40 is rotatable about its axis relative to housing 42. Translation of the end effector is provided by pivoting the shaft in two directions about the insertion point, and by sliding the shaft axially in to and out of the aperture. A drive system of instrument 38 coupled orientational movement of the end effector to motors of the manipulator arm, as described in more detail in U.S. patent application Ser. No. 09/418,726 filed on Dec. 6, 1999, entitled Surgical Robotic Tools, Data Architecture, And Use and published as PCT Publication No. WO 00/33755, the full disclosure of which are incorporated by reference.

Figure 4:
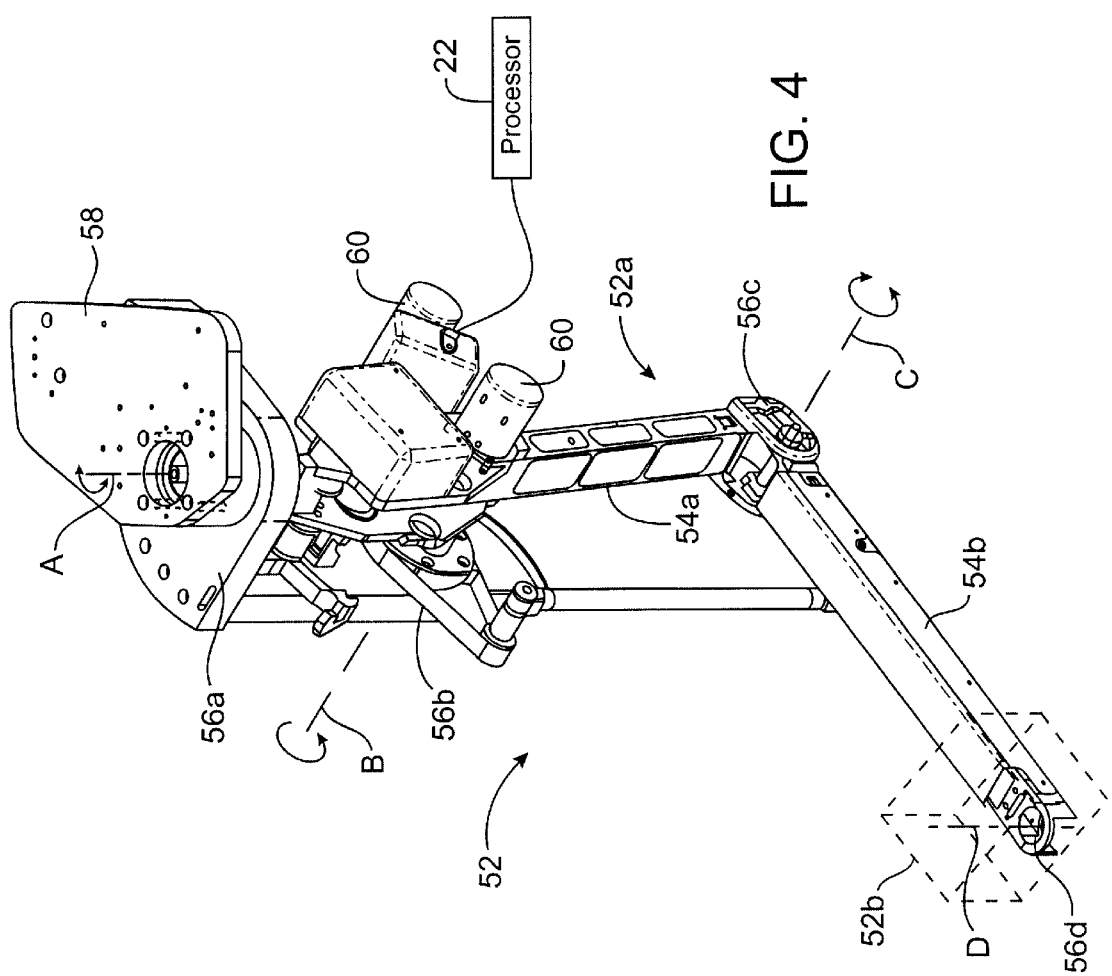
FIG. 4 is a perspective view illustrating an input linkage for sensing translation of an input handle, and schematically illustrating mounting of a gimbal assembly for sensing orientation of an input handle, for use in the master control station of FIG. 1.
Figure 5:
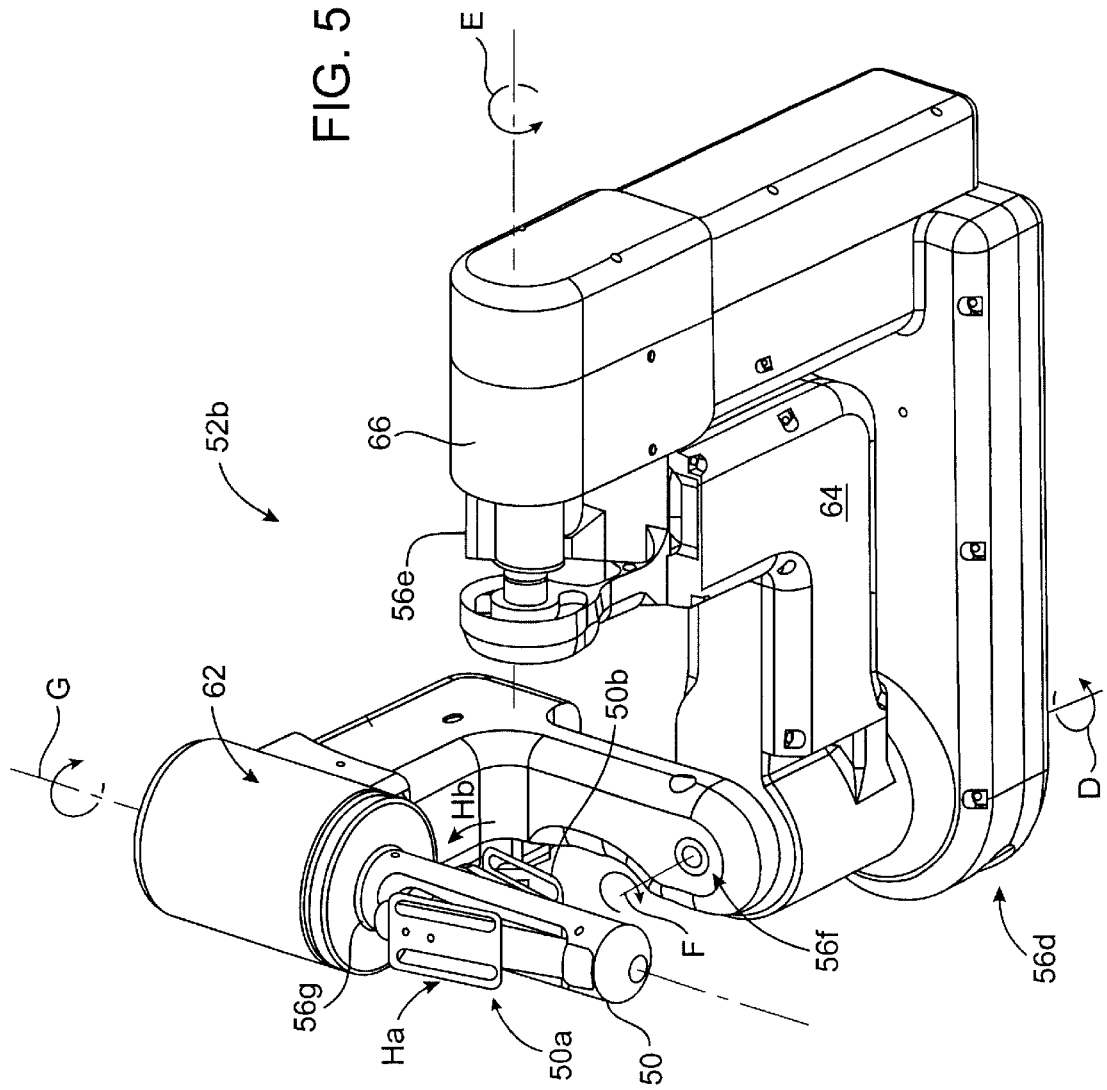
FIG. 5 is a perspective view of an exemplary gimbaled device pivotally supporting a handle for mounting on the input arm of FIG. 4.

Returning now to the input side of the robotic surgical apparatus, FIGS. 4 and 5 generally illustrate the input devices for moving end effectors 46 and for actuating the end effectors, for example, by opening and closing the end effector jaws. In broad terms, a handle 50 (see FIG. 5) is supported by a linkage 52 having joints to accommodate movement of the handle in both translation and orientation. Linkage 52 includes an arm 52a (see FIG. 4) which primarily accommodates translation of handle 50, and a gimbal 52b (see FIG. 5) which primarily accommodates and senses changes in orientation of the handle. Arm 52a includes links 54a, 54b coupled by rotational joints 56a–56c, and a mounting plate 58 for mounting to control station 10 below display 12. Motors 60 drivingly engage joints 56a–56c of arm 52a, with the motors generally being mounted near mounting plate 58 to help minimize inertia of the overall input system. The motors are controlled by processor 22, and generally provide feedback to the physician to indicate the forces being applied to end effector 46 by the surgical environment, often via a reciprocal master/slave control arrangement.

As seen most clearly in FIG. 5, gimbal 52b includes first, second, and third gimbal members 62, 64, and 66 (here counting from handle 50), with the third gimbal member being rotationally mounted to arm 52a. Handle 50 is rotatably supported by first gimbal member 62 using a rotational joint 56g, while first gimbal member 62 is, in turn, rotatably supported by second gimbal member 64 using yet another rotational joint 56f. Similarly, second gimbal member 64 is rotatably supported by third gimbal member 66 using a final rotational joint 56d, so that handle 50 is moveable with three degrees of freedom, and so that the gimbal structure supporting the handle has a redundant orientational degree of freedom. As described in more detail in U.S. patent application Ser. No. 60/111,710 filed on Dec. 8, 1998, entitled Master Having Redundant Degrees of Freedom, the full disclosure of which is incorporated herein by reference, this redundant degree of freedom can be actively driven by processor 22 so as to avoid binding of the gimbal linkage, thereby providing a large range of motion to input handle 50. The degrees of freedom of the exemplary master control of FIGS. 4 and 5 are indicated by the arrows of axes A–G in these figures. The "pinching" or grasping degree of freedom is indicated by Arrows Ha, Hb regarding grips 50a, 50b.

Figure 6:
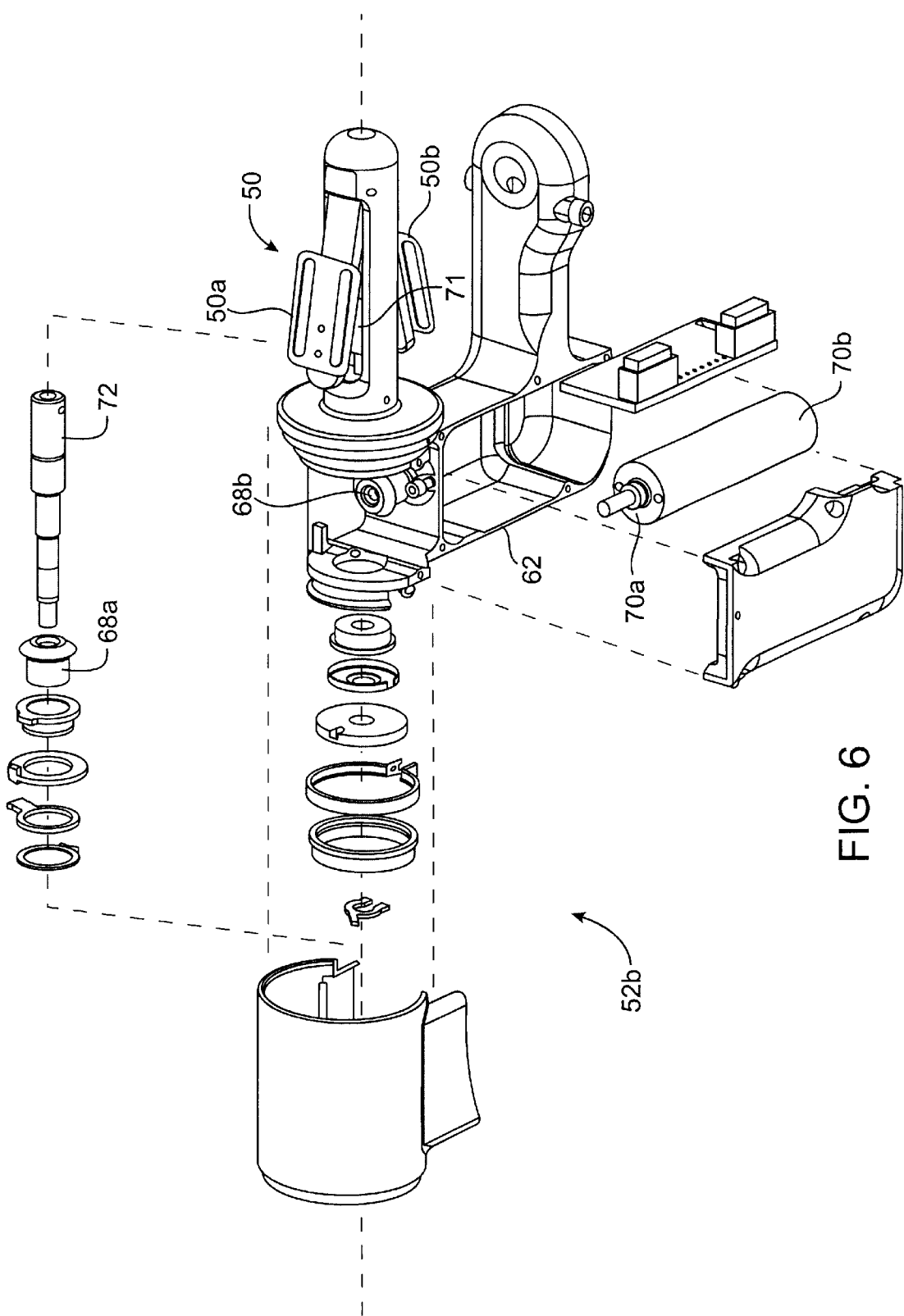
FIG. 6 is an exploded view showing internal components of the gimbal member adjacent at the input handle in the gimbal assembly of FIG. 5.

Referring now to FIGS. 5 and 6, the system operator will generally input a command to actuate a surgical end effector by squeezing first and second grip members 50a, 50b, together. It is possible to sense this input by mounting a sensor directly to handle 50, such as a Hall effect transducer, a potentiometer, an encoder, or the like. While such an arrangement can accurately transmit the actuation input to processor 22, wires extending from handle 50 and along the grip members can limit rotation of the handle about the rotational joint coupling the handle to first gimbal member 62.

As illustrated in FIG. 6, the exemplary gimbal structure includes bevel gears 68a, 68b which rotationally couple handle 50 to a motor/potentiometer 70a, 70b disposed within first gimbal member 62. While it is possible to extend wires (not shown) from an alternative actuation sensor 71 to first gimbal member 62 by allowing the wires to wind and unwind about shaft 72 extending along the axis of handle 50, a total amount of rotation will often be limited by the length of wire. Sliding electrical connections and the like, may also be possible, but may have less reliability than is desired.

As illustrated in FIG. 7, to avoid winding and unwinding of wires during rotation of handle 50, a remote sensing assembly 86 for sensing of handle actuation is mounted to first gimbal member 62, rather than to handle 50 in this maters device embodiment 53a. Handle 50 comprises a tubular structure defining an axis 74 and including first and second grip members 50a, 50b. The first and second grip members are adapted to be squeezed together by a hand of an operator so as to define a variable grip separation. The grip separation is here configured as a variable grip angle, but may alternatively comprise a variable grip separation distance, or the like. Alternative handle actuations, such as movement of a thumbwheel or knob may also be provided.

Handle 50 generally defines a proximal end 76 and a distal end 78 along axis 74. Distal end 78 of handle 50 axially receives a shaft 80 supported by first gimbal member 62 within the tubular handle structure, and the handle and shaft are releasably secured together with a quick-disconnect 82. It will be appreciated that a wide variety of detachable interface structures might be used to releasably secure handle 50 to shaft 80, including threaded connections, spring-loaded key/slot connections, latches, or the like. An actuation indicator extends distally from handle 50, the actuation indicator here in the form of a compression rod 84, sometimes called a push rod in the description below. Push rod 84 is received co-axially within a lumen of shaft 80, and mechanically couples grip elements 50a, 50b to sensor assembly 86, which is mounted to the first gimbal member 62. Push rod 84 includes a distally oriented surface 88 which engages a proximally oriented surface 90 of sensor assembly 86 when push rod 84 is moved as shown in Arrow I, and a biasing mechanism such as spring 92 urges the proximally and distally oriented surfaces against each other when handle 50 is mounted to first grip member 62. Advantageously, this arrangement provides mechanical coupling between the sensor assembly and gimbal member 62 whenever handle 50 is mounted to gimbal member 62, without having to independently attach the push rod to the sensor. Biasing spring 92 may be a linear or non-linear elastic device biasing against the depression of grip members 50a, 50b, e.g., a single or multiple element assembly including springs or other elastic members. For example, spring 92 may comprise a concentric dual spring assembly whereby one spring provides a "softer" bias response as the grips 50a, 50b are initially depressed, and a second spring provides a superimposed "firm" bias response as the grips 50a, 50b approach a fully depressed state. Such a non-linear bias may provide a pseudo force-feedback to the operator.

Optionally, active force feedback mechanisms may be included in master 52a, 52b, e.g., activated by torque or stress sensors in the slave instrument. Various other types of feedback signal devices (not shown) may alternatively or additionally be included, such as devices providing auditory, visual or vibratory signals to the operator. Note that conventional electrical connectors and wiring for sensors, motors and the like are omitted from FIG. 7A for clarity and simplicity.

In the exemplary embodiment, sensor assembly 86 further includes a circuit board 94 on which first and second Hall effect sensors, HE1, HE2 are mounted. A magnet 96 is disposed distally beyond circuit board 94 and the Hall effect sensors, while a magnetic mass 98 is axially coupled to proximally oriented surface 90 so that the magnetic mass moves (as shown by Arrow J) with the push rod and varies the magnetic field at the Hall effect sensors in response actuation of the grip members. Advantageously, both the magnet and magnetic mass are included in sensor assembly 86, so that these structures need not be independently provided (and accurately calibrated) for each handle/push rod assembly.

Figure 7A:
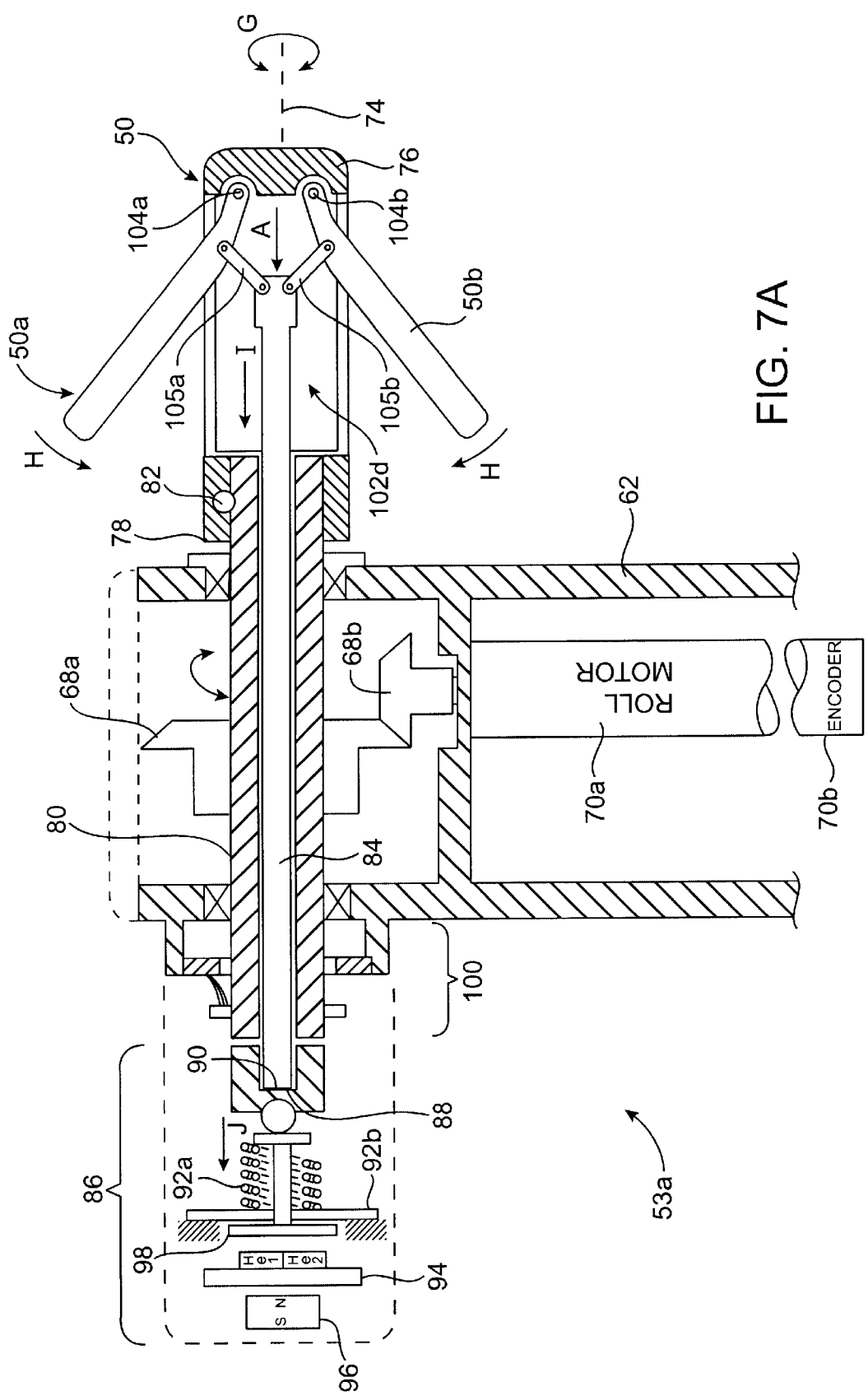
FIG. 7A is a cross-sectional view schematically illustrating mounting of a sensor on a member of a gimbal and a mechanical actuation indicator which moves relative to the sensor so that the sensor can detect gripping actuation of the handle, allowing the handle unlimited rotation relative to the member and facilitating decoupling of the handle from the gimbal assembly for removal and replacement.

In the arrangement illustrated in FIG. 7A, shaft 80 and cooperating bevel gears 68a, 68b remain in place when handle 50 is removed and replaced. This avoids repeatedly disassembling the shaft bearings which support the shaft relative to gimbal member 62. Rotational positioning of handle 50 about axis 74 may be sensed using a potentiometer or encoder included in motor 70, and/or by a separate roll sensor coupled directly to shaft 80, such as potentiometer 100. As sensor assembly 86 need not rotate with handle 50, no wires need extend from gimbal member 62 to the handle to sense actuation of the handle, so that the handle is free to rotate by an unlimited amount in either direction. As can be understood from the above description, quick-disconnect 82 rotationally affixes handle 50 to shaft 80, while push rod 84 provides a mechanical actuation signal which is transmitted co-axially with the axis of rotation of the handle so that actuation of the handle remains substantially independent of roll inputs.

While the exemplary embodiment moves push rod 84 axially during actuation, alternative embodiments might rely on differential rotation of a mechanical actuation indicator along the axis between the indicator and shaft 80, tensioning of a tensionable member, or the like.

A variety of push rod mechanisms 102 might be used to mechanically couple grip members 50 with push rod 84 (or other mechanical actuation indicators). Preferably, push rod mechanism 102a moves push rod 84 and the associated portions of sensor assembly 86 with a sufficient amount of travel to provide accurate sensing resolution, the mechanism generally providing an indicator stroke longitudinal motion (shown as Arrow I) when each of the grip members move throughout their variable separation range. In the push rod mechanism 102a example shown, grip members 50a, 50b each pivot about pivot 104a, 104b; thereby urging links 105a, 105b to move rod 84 longitudinally, as shown by Arrow A.

It should be noted that a wide variety of alternative sensing arrangements may take advantage of the mechanical actuation indication of the present invention. While Hall effect sensors are included in the exemplary embodiment, alternative embodiments may include encoders, potentiometers, or a variety of alternative optical, electrical, magnetic, or other sensing structures.

Figure 7B:
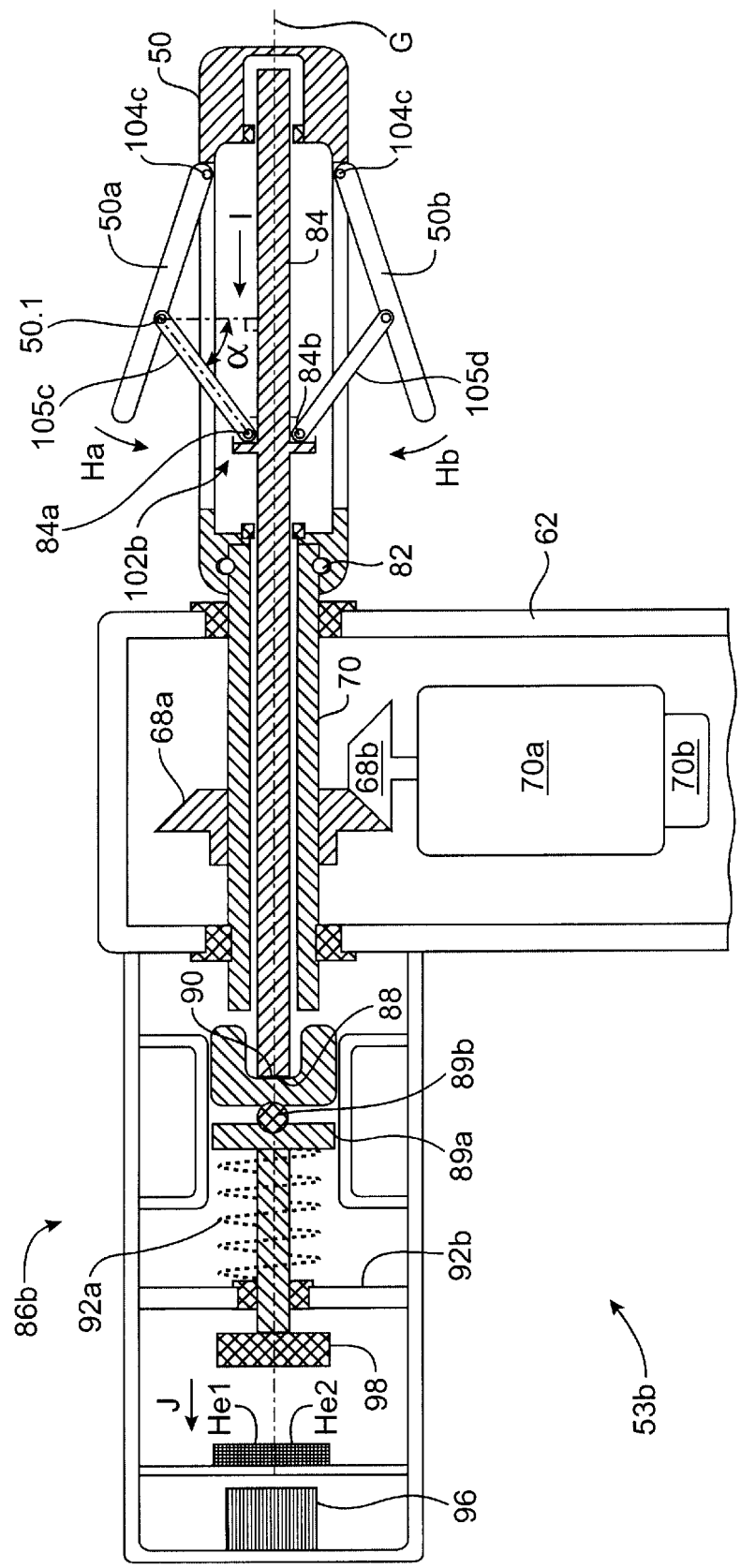
FIG. 7B illustrate an alternative embodiment of a master control device having aspects of the invention, and which is similar in many respects to that of FIG. 7A.

FIG. 7B shows an alternative embodiment of a master control device 53b similar in many respects to that of FIG. 7A. For clarity and simplicity, where components are substantially the same in FIG. 7B as those of FIG. 7A, the same reference numerals are generally used. The push rod mechanism 102b comprises grip members 50c, 50d pivoted at points 104c, 104c respectively to handle 50. The grip members 50a, 50b are coupled to push rod 84 by a diagonal links 105a, 105b respectively, the links being pivoted to the push rod at pivots 84a, 84b and to the grip members at pivots 50.1 and 50.2 respectively. The links 105c is arranged to be inclined at a variable angle α with respect to a perpendicular line connecting pivot 50.1 with push rod 84 (the opposite link 105c is likewise inclined). The geometry is preferably arranged so that the angle α remains positive throughout the range of motion of grip members 50a,b, so that the links apply a longitudinal pushing force to the push rod when the grips are depressed, the minimum value of ac being selected to avoid "locking" the grips 50a,b.

Figure 7E:
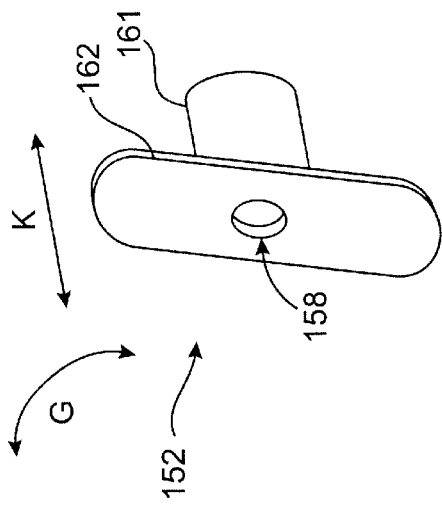
FIGS. 7D–7F are detail views of certain components of the master control device of FIG. 7C.
Figure 7D:
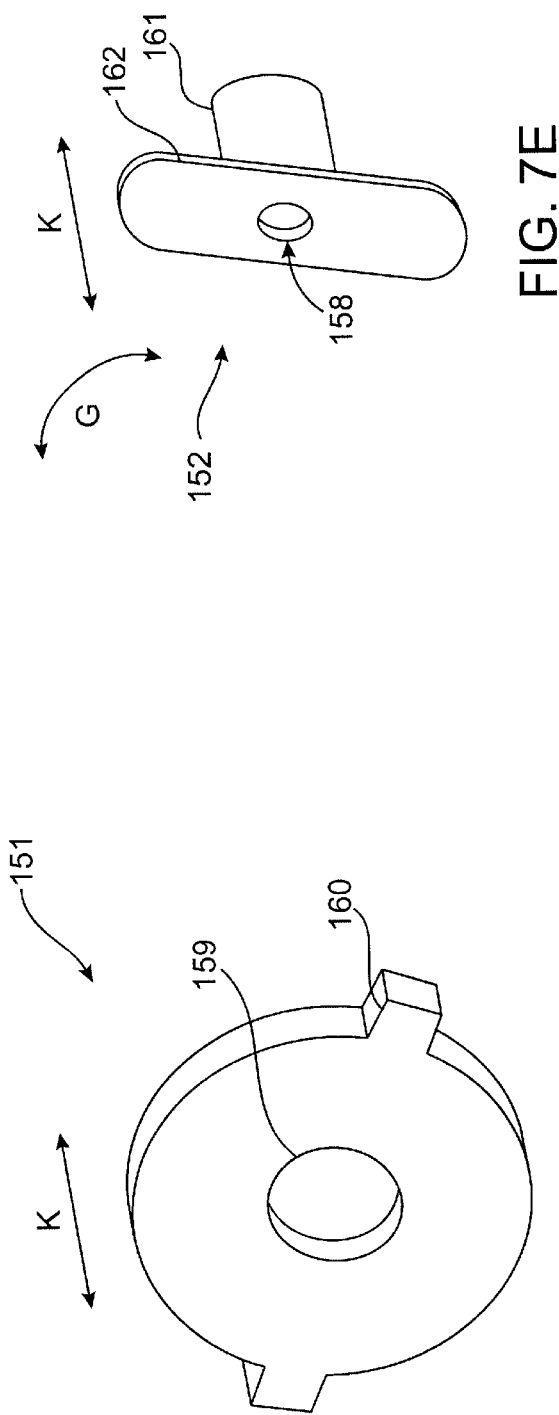
Figure 7F:
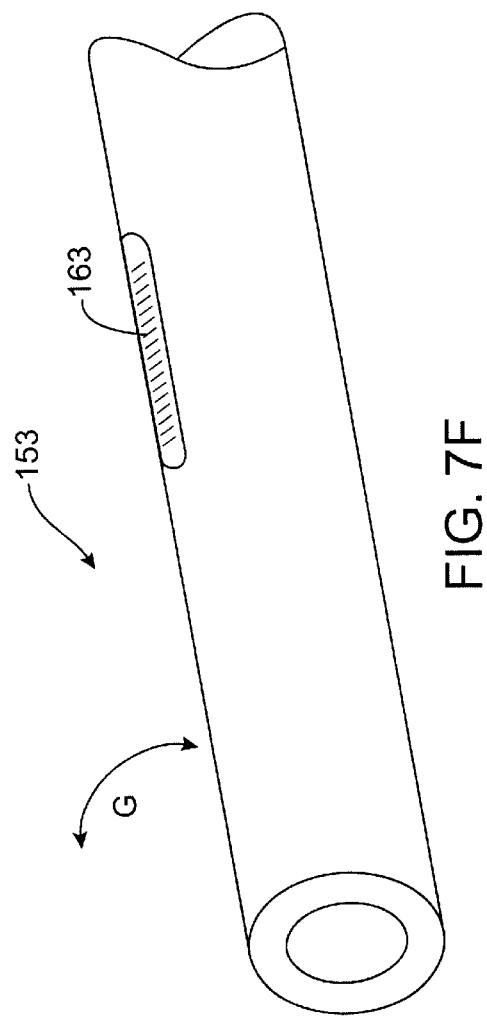

FIG. 7C illustrates an alternative embodiment 150 of a master control device having aspects of the invention, and which is similar in many respects to the examples of FIGS. 7A, 7B, and which has the sensor assembly 86c mounted adjacent the master handle 50, proximal to the gimbal member 62. For clarity and simplicity, where components are substantially the same in FIG. 7B as those of FIG. 7A, the same reference numerals are generally used. The internal portion of gimbal member 62 is omitted in FIG. 7C, being substantially similar to that of FIGS. 7A, 7B. FIGS. 7D–7F are detail views of certain components of the master control device of FIG. 7C.

The proximal sensor assembly 86c of master 150 permits a compact mounting arrangement, in which there is no added projection to the rear of gimbal member 62, and which may be mounted without inserting a comparatively long push rod (e.g., 84 in FIGS. 7A,B) through the body of gimbal 62. Thus, like the other master device embodiments described herein, a substitute master control device having the characteristics of device may be more conveniently swapped in and out, e.g., to accommodate a different type of slave instrument, surgeon preference, and the like.

Different surgical instrument types may advantageously be operatively associated with a master control handle having particular or non-standard features, such as a different ergonomic shape, a different number of degrees of freedom, additional signal devices or control buttons, different touch sensors, different feedback mechanisms, and the like. Examples of such different tools include a forceps, a needle driver, a shears, a scalpel, a bipolar cauterizer, a multiple or single element monopolar cauterizer, an ultrasonic cutting tool, an diagnostic or visualization probe, a tissue stabilizer or retractor, a clip applier, an anastomosis device, and the like.

Referring to FIGS. 7C–7F, it may be seen that the pivotally mounted grip members 50a,b is coupled via pivot links 157a, 157b to pull rod 155, and acts to pull the rod towards the handle 50 as the grips are closed or depressed. Actuator 152 is couple by threads 158 (or alternative fastening means) to pull rod 155, and thus is in turn pulled towards the handle 50 by pull-rod 155. The actuator 152 bears on magnet holder 151 which is thus is moved along the longitudinal axis of handle 50. The bias spring 156 mounted to cover 154 urges the magnet holder 151 in the opposite direction, thus permitting an oscillating axial motion of the magnet holder in the direction of Arrows K, as the grips are closed and opened. Magnet 96 is mounted to magnet holder 151. Hall effect sensor HE is mounted adjacent to adjacent to magnet 96 and is arranged in a variable spaced configuration with respect to the magnet, so that the space between magnet 96 and Hall effect sensor HE varies as the magnet holder oscillates as shown by Arrows K.

Note that in the example shown, the sensor HE is mounted distally (from the perspective of the surgeon's hand) from magnet 96 to the surface of gimbal member 62, so that the sensor-magnet spacing increases as the grips are depressed. Alternatively (not shown), the sensor HE may be mounted proximally to magnet 96, e.g., to the inner surface of cover 154, so that the sensor-magnet spacing decreases as the grips are depressed. The relationship of sensor output signal to grip position may be calibrated and adjusted for sign by the robotic servo control system.

The magnet holder 151 has an inner aperture 159 which fits over and clears the outer surface of shaft 153, to permit axial movement of the magnet holder 151. The magnet holder is prevented from rotational movement relative to gimbal 62, e.g. holder 151 may have one or more tabs 160 which engage longitudinal slots (not shown) in cover 154, preventing rotational movement of holder 151 while permitting axial motion.

Actuator 152 is slidably mounted within hollow shaft 153 by engagement portion 161. The actuator 152 comprises one or more flanges 162 which project through a corresponding one or more axial slots 163 in shaft 153, thus permitting axial movement of actuator 152 relative to shaft 153 (Arrows K). The flanges 162 bear on magnet holder 151, but are free to slide against the surface of holder 151, thus permitting rotational movement of actuator 152 relative to holder 151 (Arrows G).

The master control 150 may be mounted by screwing the threaded distal end of rod 155 into threaded hole 163 of actuator 152, and fixing the handle 50 to shaft 153 by releasable fastening or quick-disconnect handle interface 82.

Figure 8:
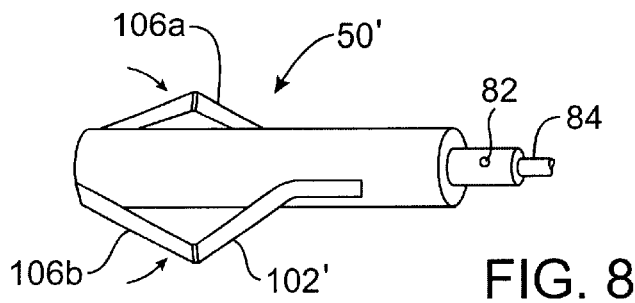
FIGS. 8–11 illustrate alternative mechanisms for mechanically coupling an actuation indicator to a pair of gripping members so that actuating the gripping members moves the indicator axially relative to a joint supporting the handle.
Figure 9:
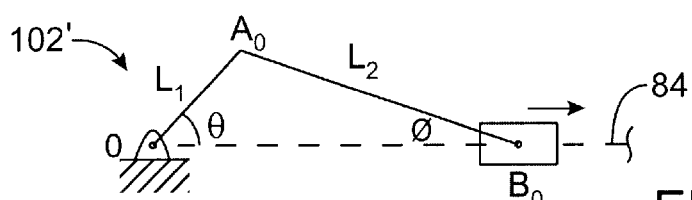

FIGS. 8 and 9 show an alternative handle assembly 50' having an alternative actuation mechanism. In this embodiment, simple flexure grip members 106a, 106b include living hinges which actuate the push rod. Handle 50' includes an extension which is receivable within a shaft mounted to first grip member 62, and can be affixed within the shaft using a quick-disconnect 82 as described above. The lengths $L_1$, $L_2$ of the substantially rigid flexure grip members 106a, 106b between hinge points O, $A_o$, and $B_o$, define actuation angles $\theta$ and $\phi$, thereby defining the actuation stroke of push rod 84.

Figure 10:
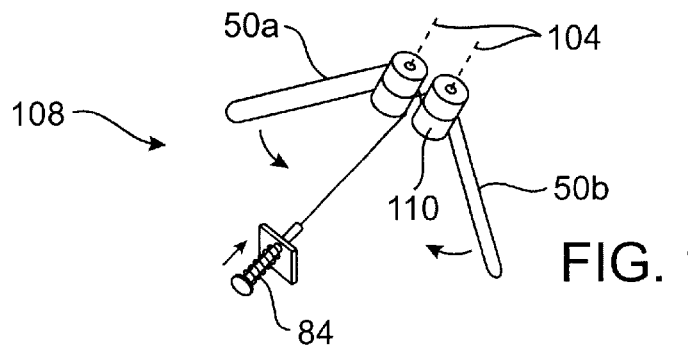

FIG. 10 shows still a further alternative actuation indication coupling mechanism is illustrated in FIG. 10. In this embodiment, gripping members 50a, 50b are synchronized with cables 110 so that the two grip members maintain a substantially equal angle with the access of the handle during an actuation stroke. A cable also effects axial movement of push rod 84, or may be directly attached to the sensor assembly.

Figure 11:
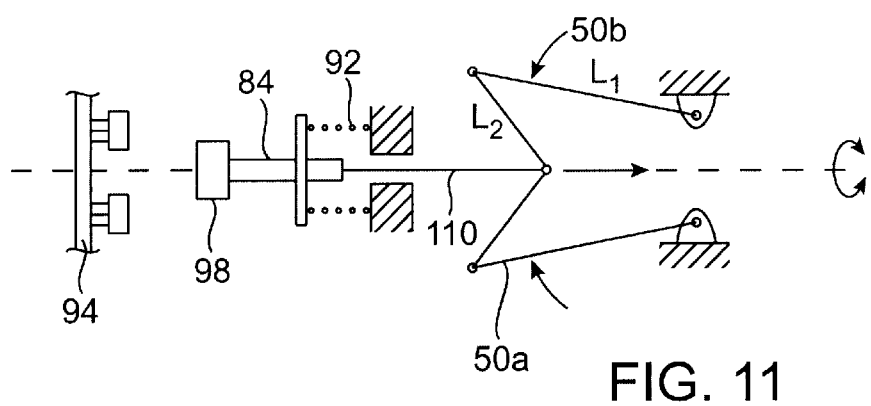

FIG. 11 shows an alternative actuator mechanism similar to that of FIG. 10, which causes axial movement of cable 110 by deflecting rigid elements having lengths $L_1$, $L_2$, similar to the flexure mechanism described above.

Figure 12:
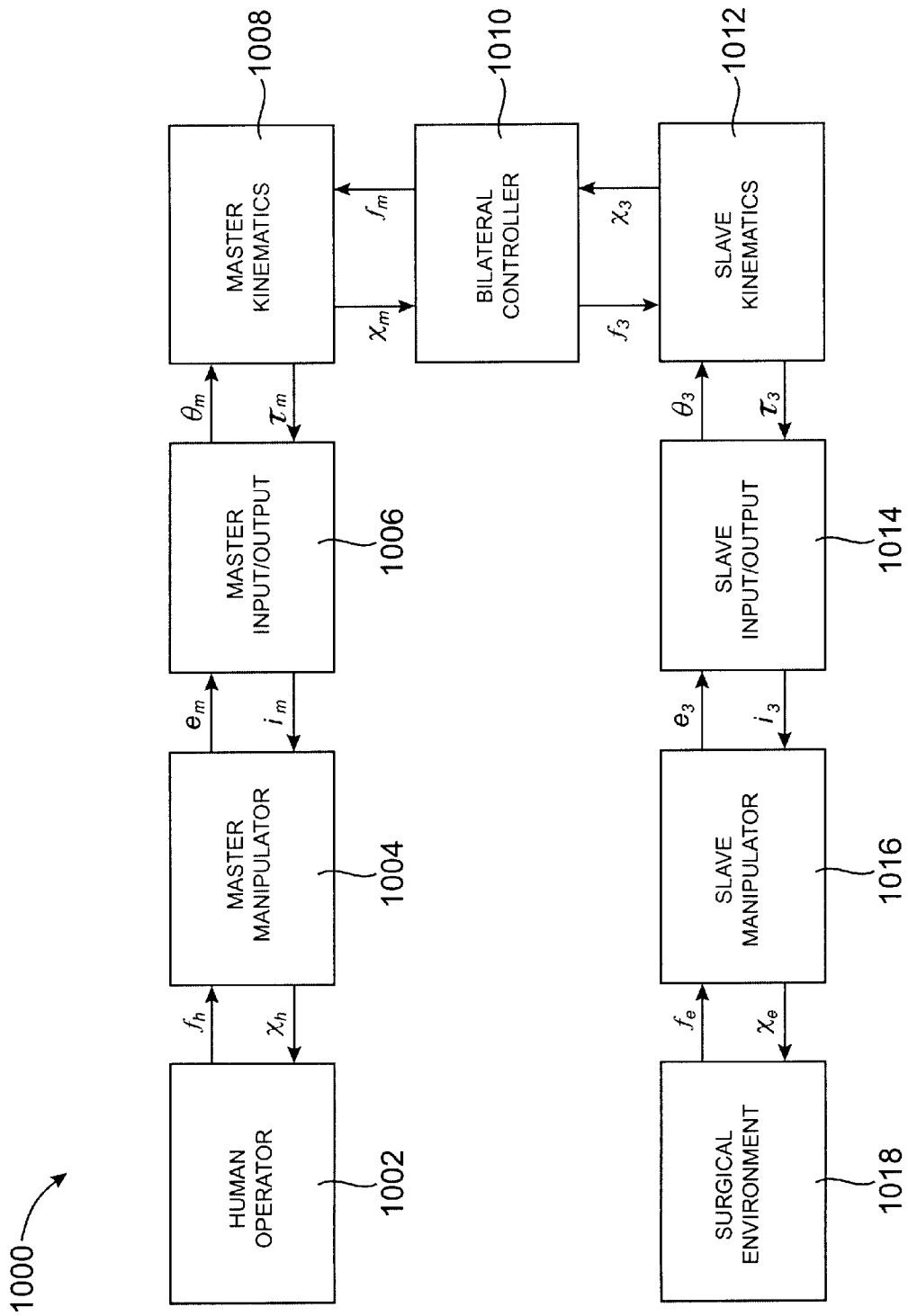
FIG. 12 schematically illustrates a force-reflecting master/slave control arrangement according to the principles of the present invention.

FIG. 12 schematically illustrates a high level control architecture for a master/slave robotic system 1000. Beginning at the operator input, a surgeon 1002 moves an input device of a master manipulator 1004 by applying manual or human forces $f_h$ against the input device. Encoders of master manipulator 1004 generate master encoder signals $e_m$ which are interpreted by a master input/output processor 1006 to determine the master joint positions $\theta_m$. The master joint positions are used to generate Cartesian positions of the input device of the master $x_m$ using a master kinematics model 1008.

Starting now with the input from the surgical environment 1018, the tissue structures in the surgical workspace will impose forces $f_e$ against a surgical end effector (and possibly against other elements of the tool and/or manipulator). Environmental forces $f_e$ from the surgical environment 1018 alter position of the slave 1016, thereby altering slave encoder values $e_s$ transmitted to the slave input/output processor 1014. Slave input/output processor 1014 interprets the slave encoder values to determine joint positions $\theta_s$, which are then used to generate Cartesian slave position signals $x_s$ according to the slave kinematics processing block 1012.

The master and slave Cartesian positions $x_m$, $x_s$ are input into bilateral controller 1010, which uses these inputs to generate the desired Cartesian forces to be applied by the slave $f_s$ so that the surgeon can manipulate the salve as desired to perform a surgical procedure. Additionally, bilateral controller 1010 uses the Cartesian master and slave positions $x_m$, $x_s$ to generate the desired Cartesian forces to be applied by the master $f_m$ so as to provide force feedback to the surgeon.

In general, bilateral controller 1010 will generate the slave and master forces $f_s$, $f_m$ by mapping the Cartesian position of the master in the master controller workspace with the Cartesian position of the end effector in the surgical workspace according to a transformation. Preferably, the control system 1000 will derive the transformation in response to state variable signals provided from the imaging system so that an image of the end effector in a display appears substantially connected to the input device. These state variables will generally indicate the Cartesian position of the field of view from the image capture device, as supplied by the slave manipulators supporting the image capture device. Hence, coupling of the image capture manipulator and slave end effector manipulator is beneficial for deriving this transformation. Clearly, bilateral controller 1010 may be used to control more than one slave arm, and/or may be provided with additional inputs.

Based generally on the difference in position between the master and the slave in the mapped workspace, bilateral controller 1010 generates Cartesian slave force $f_s$ to urge the slave to follow the position of the master. The slave kinematics 1012 are used to interpret the Cartesian slave forces $f_s$ to generate joint torques of the slave $\tau_s$ which will result in the desired forces at the end effector. Slave input/output processor 1014 uses these joint torques to calculate slave motor currents $i_s$, which reposition the slave $x_e$ within the surgical worksite.

The desired feedback forces from bilateral controller are similarly interpreted from Cartesian force on the master $f_m$ based on the master kinematics 1008 to generate master joint torques $\tau_s$. The master joint torques are interpreted by the master input/output controller 1006 to provide master motor current $i_m$ to the master manipulator 1004, which changes the position of the hand held input device $x_h$ in the surgeon's hand.

It will be recognized that the control system 1000 illustrated in FIG. 12 is a simplification. For example, the surgeon does not only apply forces against the master input device, but also moves the handle within the master workspace. Similarly, the motor current supplied to the motors of the master manipulator may not result in movement if the surgeon maintains the position of the master controller. Nonetheless, the motor currents do result in tactile force feedback to the surgeon based on the forces applied to the slave by the surgical environment. Additionally, while Cartesian coordinate mapping is preferred, the use of spherical, cylindrical, or other reference frames may provide at least some of the advantages of the invention.

Unfortunately, it is possible for the system operator or other personnel to inadvertently move handle 50 by bumping into any portion of the linkage 52 supporting the handle (see FIG. 4), or even into workstation 10 (see FIG. 1). As described above, viewing sensor 20 can avoid inadvertent actuation or movement of the handle when the system operator is not viewing the surgical site via display 12. In other words, preferably the bilateral control arrangement 1000 running on processor 22 is not enabled to an operative state unless viewing sensor 20 provides a signal indicating that the system operator is viewing the surgical site, or at least blocking light transmitted to the light sensor.

In the absence of such a signal, or in other words, when the sensor provides an alternative signal indicating that the system operator is not viewing the surgical site, the control arrangement 1000 may enter an alternative state inhibiting movement of the end effector. This may be provided by simply opening the control loop, by arbitrarily setting the forces to be applied to the slave $f_s$ to 0, or the like. Alternatively, the system can maintain the end effector and/or handle in a fixed position. Optionally, the system can avoid movement of the end effector by assuming (at least for calculation of forces to be applied by the slave $f_s$) that the position of the master controller $x_m$ remains fixed at least until the viewing sensor provides the proper viewing signal. This may help hold the end effector to a fixed location when it is not intentionally moved, which may also inhibit movement of the master by applying a return force $f_m$ toward the "fixed" master position.

PCT Application Publication No. WO 00/30548 (incorporated by reference herein) describes, among other things, methods and devices for inhibiting the motion of a robotic slave device or instrument when a corresponding master control device is not operationally associated with the slave. The instrument may be held in position using a controller signal actuating a brake system and/or by the controller providing appropriate signals to the drive motors of the slave instrument and robotic arm actuation system to inhibit movement of the slave.

For example, once the operative control between master device and slave instrument is interrupted by the controller (e.g., due to a touch sensor response, a viewer sensor response, operator input signal, and the like), the control system may cause the translational movements of the slave instrument and robotic arm to float while the orientation of the end effector is locked. In general, when movements of one or more joints of a master or slave linkage are allowed to float, the floating joints may optionally still have some forces imposed against the joint by their associated joint-drive systems, as the controller may impose actuation forces on the master and/or slave so as to compensate for gravity, friction, or the like.

In one exemplary method described in WO 00 30548, when control between master and slave is interrupted, the position of the slave in joint space immediately interruption is recorded in a memory of the robotic controller. Subsequently, the slave position in joint space is detected and compared with the pre-interruption position. If the slave has moved, the controller generates error signals corresponding to the positional deviation, and in turn determines and produces the required torques by drive motors of the slave to cause the slave to return to the pre-interruption position and orientation.

In addition to viewing sensor 20, it is also desirable to sense when the operator is touching handle 50 so that processor 22 enables the robotic surgery apparatus to an operative state only when the hand of the operator engages the handle. Conveniently, gimbal linkages 52 supporting handle 50 generally comprise links coupled by moveable joints, with at least one joint (and preferably a plurality of joints, ideally all joints) powered by motors and coupled to a position sensor, as described above. These driven and position sensing joints may be used for force reflection, actively driving handle 50 into alignment with surgical end effectors, friction and/or gravity compensation so as to avoid imposing undue forces on the system operator, and the like.

Advantageously, the driven joints of linkages 52 can be used to determine when the operator is actually touching handle 50 by introducing a low level of controlled vibration. Preferably, the vibration will be effected by at least the motor 70 coupled to a joint 56 between handle 50 and first gimbal member 62, or to the analogous joint closest to the handle in other linkage arrangements. When the operator's hand is not engaging handle 50, the handle will oscillate per the inertia, stiffness, drive joint friction, and other characteristics of the linkage/handle system. These oscillations may be sensed using the joint sensor coupled to the oscillating joint, such as potentiometer 100, the encoder of motor 70, a dedicated oscillation sensor or the like.

When an operator's hand comes in contact with the oscillating handle, the hand will alter the dynamic characteristics of the driven system, typically dampening the induced oscillations. The dampening of the oscillations will typically be sensed via the joint sensor. Hence, a signal indicating contact between the operator's hand and handle 50 may be generated by analyzing the vibrations.

Figure 13A:
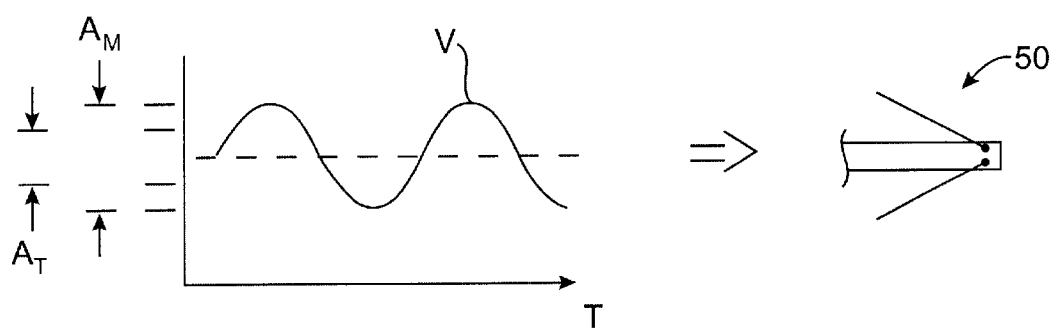
FIGS. 13A, 13B, and 14 schematically illustrate surgical robotic input handles having touch sensor systems, and methods for their use.
Figure 13B:
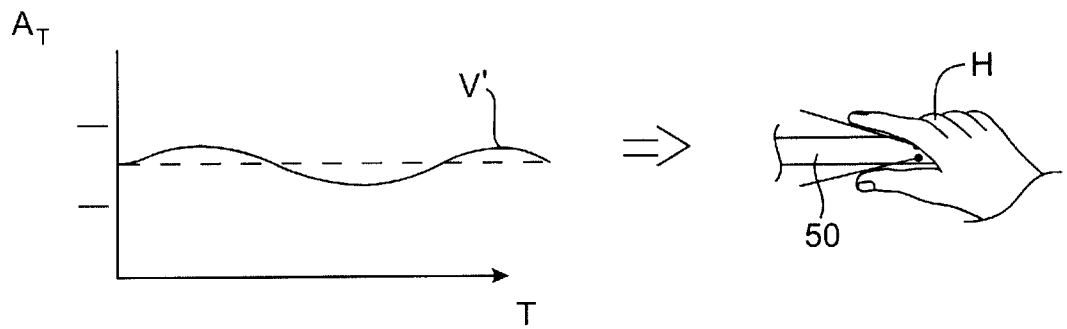

As can be understood with reference to FIGS. 13A and 13B, in an exemplary embodiment of a method for sensing contact between handle 50 and a hand H, a sinusoidal vibration is induced in handle 50 by driving joint 56 coupling the handle to first gripping member 62 using motor 70. Preferably, the induced vibration is beyond the closed-loop bandwidth of the master arm servosystem, so that the vibration is not strongly coupled to the joint and total amplitude of movement of the handle is small.

Preferably, the induced vibration frequency will be below the natural mechanical frequency of the handle itself, so that contact between hand H and handle 50 dampens the vibration and the joint position sensor measures a smaller vibration amplitude $A_m$. If induced vibration frequency is too high, the distribution of standing acoustic waves over the handle may cause the amplitude of the vibration (as measured at the sensor) to increase when the hand contacts the handle.

By inducing vibration V at a known and constant frequency, well-known synchronous-detection algorithms can be used to isolate the sensed vibration amplitude $A_m$ from sensor system noise. Preferably, the vibration level will be decreased to the point of an acceptable signal-to-noise ratio to minimize vibration perceived by the operator, particularly if the operator finds the induced vibration to be objectionable.

As seen in FIG. 13B, contact between hand H and handle 50 dampens the induced vibration to a reduced amplitude wave V. Once the measured amplitude $A_m$ is below some threshold amplitude $A_t$, a signal is generated indicating that the hand is contacting the handle, and movements of the handle can effect movements of the end effector. When the vibration exceeds the threshold amplitude, an alternative signal from the touch sensor system interrupts the master/slave control system, as described above.

While the use of driven joints to induce and measure vibrations avoids added complexity in the input system, alternative touch sensor structures may also be provided. For example, referring now to FIG. 14, a touch sensing handle 120 includes a piezoelectric transducer 122. An electric oscillator coupled to controller 22 can drive transducer 122 to cause handle 120 to vibrate. When handle 50 is touched by the hand of the surgeon, the induced vibration will be damped. Typically, the damping will be detected using the same piezoelectric transducer that drives the mechanical vibration, although separate piezoelectric vibration generators and sensors could be used.

Figure 14:
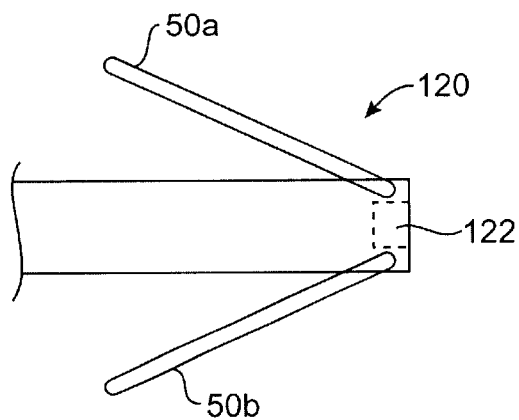

The touch sensing handle 120 illustrated in FIG. 14, like the touch sensing system described with reference to FIGS. 13A and 13B, should be able to detect if the handle is being touched, regardless of whether or not the system operator is wearing rubber gloves or the like. Additionally, the touch sensor should not be effected by objects that are near, but not touching, handle 50.

The touch sensing systems may operate at a variety of frequencies, including resonant frequencies. If the system is unable to detect contact between the operator's hand and the handle at a node when a single vibration driver is used, more than one frequency can be induced so that there is no position on the handle from which contact cannot be detected. The frequency induced by a piezoelectric transducer may be audible or ultrasonic, and the vibration may be a bulk vibration or a surface acoustic wave. In some embodiments, the transducer may be pulsed, so that the reflection from the pulse is measured. Touching the handle with the hand of the operator should produce an additional reflection. Once again, a variety of vibration inducing and sensing structures might be used, including accelerometers, and the like.

While the exemplary embodiments have been described in some detail, by way of example and for clarity of understanding, a variety of changes, adaptations and equivalents will be obvious to those of skill in the art. Hence, the scope of the invention is limited solely by the appended claims.

What is claimed is:

1. A surgical robotic input device comprising:
   a handle actuatable by a hand of an operator so as to define a variable handle input, the handle being movable to define a movement input;
   a structural member supporting the handle and pivotally engaging the handle at a joint so that the handle is rotatable about an axis relative to the member, the joint defining the axis;
   an actuation indicator extending from the handle toward the structural member, the indicator moving relative to the member in response to the actuation input, at least a portion of the indicator moving coaxially with the axis when the handle is actuated; and
   an input sensor supported by the structural member, the input sensor generating a signal in response to movement of the indicator relative to the member, the input signal being independent of rotation of the handle about the axis.

2. The surgical robotic input device of claim 1, wherein the handle is detachably mounted to the member.

3. The surgical robotic input device of claim 2, wherein the indicator detachably couples the handle to the sensor.

4. The surgical robotic input device of claim 3, wherein the indicator comprises a compression rod.

5. The surgical robotic input device of claim 4, wherein the compression rod has a proximal end adjacent the handle and a distal end adjacent the structural member, the rod having a distally oriented surface disposed adjacent the distal end, and further comprising a proximally oriented surface engageable with the distally oriented surface of the rod and coupled to the input sensor, the proximally oriented surface movable along the axis and biased toward a proximal position so as to maintain engagement between the sensor assembly and the rod and to bias the handle to an unactuated configuration.

6. The surgical robotic input device of claim 5, wherein the input sensor comprises a Hall effect sensor, and wherein the sensor assembly further comprises a magnet, a magnetic field of the magnet varying at the Hall effect sensor with the movement of the indicator.

7. The surgical robotic input device of claim 3, wherein the indicator comprises a tension element.

8. The surgical robotic input device of claim 7, wherein:
   the tension element has a proximal end adjacent the handle and a distal end adjacent the structural member, the distal end of the tension element detachably coupling to a sensor actuator element; and
   the sensor actuator element is movable along the axis and biased toward a distal position so as to maintain tension between the sensor actuator element and the tension element, so as to bias the handle to an un-actuated configuration.

9. The surgical robotic input device of claim 8, wherein the input sensor comprises a Hall effect sensor, and wherein the sensor assembly further comprises a magnet, a magnetic field of the magnet varying at the Hall effect sensor with the movement of the indicator.

10. The surgical robotic input device of claim 1, wherein the structural member is supported by a linkage so as to move with a plurality of degrees of freedom.

11. The surgical robotic input device of claim 1, wherein the handle comprises a pair of first and second grip members separated by a variable space, the actuation input comprising a change of the separation space between the grip members.

12. The surgical robotic input device of claim 1, wherein the handle comprises a pair of first and second grip members oriented at a variable angle to the axis, the actuation input comprising a change of the grip member orientation angle.

13. A surgical robotic input device comprising:
   a handle actuatable by a hand of an operator so as to define a variable handle input, the handle being movable to define a movement input;
   a structural member supporting the handle so that the handle is rotatable about an axis relative to the member;
   an actuation indicator extending from the handle toward the structural member, the indicator moving relative to the member in response to the actuation input, the handle and indicator define a fist modular handle assembly including a quick disconnect handle interface removably mounting the first assembly to the structural member;
   an input sensor supported by the structural member, the input sensor generating a signal in response to movement of the indicator relative to the member, the input signal being independent of rotation of the handle about the axis; and
   at least a second modular handle assembly including a quick-disconnect handle interface and mountable to the structural member in place of the first handle assembly.

14. The surgical robotic input device of claim 13, wherein:
   the second handle assembly differs from the first handle assembly in at least one characteristic selected from the group consisting of ergonomic shape, number of degrees of freedom, signal device, control button, touch sensor, and feedback mechanism.

15. The surgical robotic input device of claim 1, wherein the handle can rotate about the axis continuously relative to the structural member without mechanical limitation.

16. A surgical robotic input device comprising:
   a handle actuatable by a hand of an operator so as to define a variable handle input, the handle being movable to define a movement input;
   a structural member supporting the handle so that the handle is rotatable about an axis relative to the member;
   an actuation indicator extending from the handle toward the structural member, the indicator moving relative to the member in response to the actuation input;
   an input sensor supported by the structural member, the input sensor generating a signal in response to movement of the indicator relative to the member, the input signal being independent of rotation of the handle about the axis; and
   a touch sensor coupled to the handle, the touch sensor generating a touch signal in response to contact between the hand of the operator and the handle.

17. A surgical robotic apparatus for performing a surgical procedure on a patient body, the apparatus robotically moving a surgical end effector so as to effect the surgical procedure in response to movement of an input handle by a hand of an operator, the apparatus comprising:

a touch sensor system coupled to the handle, the touch system generating a first signal in response to coupling of the handle with the hand of the operator, the surgical robotic apparatus being enabled to an operative state in response to the first signal.

18. The surgical robotic apparatus of claim 17, wherein the surgical robotic apparatus is reconfigured to an alternate state when the touch system generates a second signal, the touch system generating the second signal in response to decoupling of the hand of the operator from the handle, the surgical robotic apparatus in the alternate state inhibiting movement of the end effector when the handle moves.

19. The surgical robotic apparatus of claim 17, wherein the touch system induces a vibration in the handle, and wherein the touch system senses coupling of the hand of the operator and the handle by measuring the induced vibration.

20. The surgical robotic apparatus of claim 19, wherein the touch system comprises at least one piezoelectric element.

21. The surgical robotic apparatus of claim 20, wherein the at least one piezoelectric element of the touch system comprises a piezoelectric transducer which vibrates the handle and which senses the induced vibration.

22. The surgical robotic apparatus of claim 21, wherein the at least one piezoelectric element of the touch system comprises a piezoelectric vibrator, the touch system further comprising a piezoelectric vibration sensor.

23. The surgical robotic apparatus of claim 21, wherein the touch system senses induced oscillation of the joint using a joint actuation sensor coupled to the joint.

24. The surgical robotic apparatus of claim 19, wherein the touch system oscillates a joint motor driving a joint supporting the handle.

25. The surgical robotic apparatus of claim 17, further comprising:

a display viewable by the system operator for directing the surgical procedure; and a view sensor system, the view sensor system generating a third signal when the operator is viewing the display and a fourth signal when the operator is not viewing the display;

wherein the surgical robotic apparatus is enabled to the operative state in response to the third signal and is reconfigured to an alternate state in response to the fourth signal.

26. A method for controlling a robotic system, the robotic system including a first input handle, the handle being movable and actuatable by an operator's hand, the method comprising:

inputting commands to the robotic system by:

moving the handle with the hand so as to articulate a pivotal joint of the system; and by actuating the handle with the hand so as to mechanically transmit an actuation signal across the joint to an actuation sensor of the system;

sensing movement of the handle by measuring articulation of the joint;

sensing actuation of the handle by measuring the mechanically transmitted actuation signal with the actuation sensor; and moving an end effector in response to the measured articulation of the joint, and in response to the measured actuation signal.

27. The method of claim 26, wherein the mechanically transmitting step comprises moving a compression rod coaxially with an axis of the joint.

28. The method of claim 26, wherein the mechanically transmitting step comprises moving a tension element coaxially with an axis of the joint.

29. The method of claim 27, wherein the handle movement input step is performed employing a handle support structure which can accommodate unlimited rotation of the handle about the axis.

30. The method of claim 26, further comprising:

removing the first handle;

replacing the first handle with an alternative handle, and moving the end effector in response to movement and actuation of the alternative handle.

31. The method of claim 30, further comprising providing the alternative handle with at least one different characteristic than the first handle.

32. A robotic method comprising:

enabling a robotic apparatus to an operative state in response to coupling of a handle of the robotic apparatus with a hand of a system operator;

inputting commands to the robotic apparatus by moving the handle with the hand of the operator;

moving an end effector in response to the input commands; and reconfiguring the robotic apparatus to an alternate state in response to decoupling of the hand of the operator from the handle, so as to inhibit inadvertent movement of the end effector.

* * * * *